United States Patent [19]
Sasaki et al.

[11] Patent Number: 5,824,777
[45] Date of Patent: Oct. 20, 1998

[54] ATTENUATED MEASLES VIRUS VACCINE CONTAINING SPECIFIC NUCLEOTIDE SEQUENCE AND A METHOD FOR ITS ABSOLUTE IDENTIFICATION

[75] Inventors: Keiko Sasaki; Takayuki Mori; Satoshi Makino, all of Tokyo, Japan

[73] Assignee: The Kitasato Institute, Tokyo, Japan

[21] Appl. No.: 905,817

[22] Filed: Aug. 4, 1997

Related U.S. Application Data

[62] Division of Ser. No. 348,891, Nov. 25, 1994, Pat. No. 5,654,136, which is a continuation of Ser. No. 848,400, Mar. 10, 1992, abandoned.

[30] Foreign Application Priority Data

Oct. 14, 1991 [JP] Japan ................................ 3-293625

[51] Int. Cl.$^6$ .................................................. C07K 14/12
[52] U.S. Cl. ........................ 530/350; 530/403; 435/235.1
[58] Field of Search .................................. 530/350, 403; 435/235.1

[56] References Cited

U.S. PATENT DOCUMENTS 4,617,261  10/1986  Sheldon, III et al. .
4,985,244   1/1991  Makino et al. .

FOREIGN PATENT DOCUMENTS 0 440 219  8/1991  European Pat. Off. .

OTHER PUBLICATIONS

Enders, J., et al., "Propagation in Tissue Cultures of Cytopathogenic Agents from Patients with Measles", *Cytopathogenic Agents from Measles Cases*, pp. 277–286.

Enders, J., et al., "Studies on an Attenuated Measles–Virus Vaccine", *New England Journal of Medicine*, vol. 263, 1960, pp. 153–184.

Makino, S., et al., "Cultivation of Measures Virus in Sheep Kidney Cells", *Japan J. Microbiol.*, vol. 14, No. 6, 1970, pp. 501–504.

Makino, S., et al., "Field Trial with a Further Attenuated Live Measles Virus Vaccine", *Japan J. Microbiol.*, vol. 17, No. 1, 1973, pp. 75–79.

Sasaki, K., "Studies on the Modification of the Live AIK Measles Vaccine", *Kitasato Arch. of Exp. Med.*, vol. 47, Nos. 1–2, 1974, pp. 1–12.

Makino, S., et al., "Studies on the Modification of the Live AIK Measles Vaccine", *Kitasato Arch. of Exp. Med.*, vol. 47, Nos. 1–2, 1974, pp. 13–21.

Hirayama, M., "Measles Vaccine Used in Japan", *Reviews of Infectious Diseases*, vol. 5, No. 3, May–Jun. 1983, pp. 495–503.

Makino, S., "Development and Characteristics of Live AIK–C Measles Virus Vaccine, A Brief Report", *Reviews of Infectious Diseases*, vol. 5, No. 3, May–Jun. 1983, pp. 504–505.

Cattaneo, R., et al., Abstract and Sequence Search Results, *Virology*, vol. 173, No. 2, 415–25, Dec. 1984, pp. 1–31.

Schmid, A., et al., "A Procedure for Selective Full Length cDNA Cloning of Specific RNA Species", 1987, vol. 15, No. 10, pp. 3987–3996.

Mack, D., et al., "Novel Viruses", *PCR Protocols: A Guide to Methods and Applications*, 1990, pp. 378–385.

*Primary Examiner*—Scott W. Houtteman
*Attorney, Agent, or Firm*—Young & Thompson

[57] ABSTRACT

A measles vaccine virus AIK-C strain comprises genomic RNA that produces by reverse transcription cDNA having a specific nucleotide sequence indicative of the viral genomic RNA in the seed virus for measles vaccine or measles virus vaccine. The complete sequence of 15,894 nucleotides has been determined.

7 Claims, 3 Drawing Sheets

FIG. 3

| PRIMER | BASE SEQUENCE | OBTAINED cDNA |
|---|---|---|
| MP-1: | 5'—TTAGGGATATCCGAGATGGCCACAC—3' | pMN2 |
| MP-2: | 5'—CTCGGAAGAACAAGGCTCAGACAC—3' | pMP1 |
| MP-3: | 5'—GGAAGGACACCTCTCAAGCATCATG—3' | pMM1 |
| MP-4: | 5'—GCAGCCATCAGTTCCTCAAG—3' | pMF1 |
| MP-5: | 5'—GTCTACATCCTGATTGCAGTG—3' | pMH1 |
| MP-6: | 5'—GTCAACGAGGAAGATCCGTGAACTCCTCA—3' | pML1 |
| MP-7: | 5'—GCACGATTTGACTAAGGCACTCCA—3' | pML2 |
| MP-8: | 5'—TGTCCTCATTGACAAAGAGTCATG—3' | pML3 |
| MP-9: | 5'—AGGTGCTTGTCAATGCTCTGCTCCTAAGCCA—3' | pML4 |
| MP-10: | 5'—CTTATCGATGGCTCTGCTCCTGGGC—3' | pML5 |
| MP-11: | 5'—TGGAAGCTTATCCAGAATCTCAAGTCCGGCT—3' | pML6 |
| BEP(dT)7: | 5'—CTGTGAATTCTGCAGGATCCTTTTTT—3' | pMN1 |

ATTENUATED MEASLES VIRUS VACCINE CONTAINING SPECIFIC NUCLEOTIDE SEQUENCE AND A METHOD FOR ITS ABSOLUTE IDENTIFICATION

This application is a division of application Ser. No. 08/348,891, filed Nov. 25, 1994, now U.S. Pat. No. 5,654,136 which is a continuation application under 37 CFR §1.62 of application Ser. No. 07/848,400, filed Mar. 10, 1992, now abandoned.

BACKGROUND OF THE INVENTION

1. Field of the Invention

The present invention relates to a strain of measles virus vaccine comprising a specific nucleotide sequence, and a method for its absolute identification.

2. Description of the Prior Art

Measles virus is the causative virus of measles, and belongs to the Paramyxoviridae family of RNA virus.

The first isolation of measles virus from patients using a primary culture of human kidney cells was made by J. F. Enders et al. in 1954 (Enders, J. F. et al., *Proc. Soc. Exp. Biol. Med.*, Vol. 86, pp. 227–286, 1954). Attenuated measles virus vaccine was developed using the isolated Edmonston strain by Enders et al. (Enders, J. F. et al., *New England J. Med.*, Vol. 263, pp. 153–259, 1960). However, the vaccine developed by Enders et al. frequently induced adverse effects including pyrogenicity and exanthema.

Many strains of attenuated measles virus having been established by further attenuation of the Edmonston strain. Among these strains the Schwarz strain established by A. J. F. Schwarz has been commonly used for live measles vaccines.

The present inventors have isolated four strains of a cold variant derived from attenuated measles virus of the Edmonston strain, supplied by Dr. Enders (Makino, S. et al., *Jap. J. Microbiol.*, Vol 14, pp. 501–504, 1970).

Reduction of immunogenicity, i.e. effectiveness, according to a development of attenuation of measles virus has generally been known. Among the strains of the isolated cold variant, a viral strain which grows adaptively at 33° C. was found to be a further attenuated measles virus with high immunogenicity having properties different from those generally observed in the conventional measles virus (Makino, S. et al., *Jap. J. Microbiol.*, Vol. 17, pp. 75–79, 1973).

In order to develop the seeds for live measles vaccines from the cold variant, one of the present inventors has isolated clone virus which is a strain adapted with chick embryo cells obtained from specific pathogen-free eggs, having the same temperature marker, and designated as the AIK-C strain (Sasaki K., *Kitasato Arch. Exp. Med.*, Vol. 47, pp. 1–12, 1974).

The pyrogenicity ratio ($\leq 37.5°$ C.) of an AIK-C strain live vaccine produced from the seeds of AIK-C strain in measles-sensitive infants approximately ⅓–¼ as compared with that of Schwarz strain vaccine. The AIK-C strain has been found to be a further attenuated measles virus than the Schwarz strain, with the unique characteristic of having a high immunogenicity response without lowering immunogenicity (Makino, S. et al., *Kitasato Arch. Exp. Med.*, Vol. 47, pp. 13–21, 1974).

Encephalitis that seems to be caused by administered live measles vaccine has been observed in 1–3 persons per million treated infants. However, this neurological complication has never been reported in the case of the AIK-C strain in spite of the administration of AIK-C strain live measles vaccine to ten million people in Japan (Hirayama, M. et al., *Inf. Dis.*, Vol. 5, pp. 495–503, 1983; Makino, S., Vol. 5, pp. 504–505, 1983).

SUMMARY AND OBJECTS OF THE INVENTION

The biological properties of the AIK-C strain are unique, and differ markedly from those of the other strains of measles virus. However, the virus is easily mutated and even in an attenuated measles virus strain such as the AIK-C strain, a small degree of formation of variant strains can be observed during the growth phase. Accordingly, during the production of live measles vaccine, the quality control for comparing the respective identities of the seed virus and the vaccine virus produced therefrom is the most important procedure.

As noted above, a temperature marker test for the AIK-C strain has been applied as a quality control test (Sasaki, K., *Kitasato Arch. Exp. Med.*, Vol. 47, pp. 1–12, 1974). However that biological assay method does not always provide absolute identification of the AIK-C strain.

The fundamental biological properties of the virus depend on its genome, which consist of nucleic acid of viral particles. The nucleic acid of measles virus consists of single strain (-)RNA, and each viral strain has its own nucleic acid made up of a specific nucleotide sequence.

Complete differential identification between viral strains is, therefore, necessary to determine the nucleotide sequence of viral nucleic acid in the strain. The present inventors have focused on this point, and have analyzed the nucleotide sequence of nucleic acid relating to measles virus infection. In the course of that analysis, the inventors have provided an administrative control method for producing a stable AIK-C strain of measles virus without variants or mutation.

The known identification methods for various measles strain apply a specific biological response test for the virus strain in question; however, these are not methods capable of absolute identification. For quality control during production of the AIK-C strain vaccine, the aforementioned temperature marker test has been applied. The present inventors, on the other hand, have determined the entire nucleotide sequence of the AIK-C strain virus genome, thereby to establish an absolute identification method for the said identification test. Since the entire specific nucleotide sequence, consisting of 15,894 bases in AIK-C strain, has been clearly determined, the virus can be identified at the genetic level, and the identification technique can therefore provide an absolute determination, so that quality control on a stable AIK-C strain vaccine can easily and exactly be performed.

Therefore an object of the present invention is to provide an attenuated live measles vaccine comprising a specific nucleotide sequence.

Another object of the present invention is to provide an absolute identification method for a measles virus strain.

A further object according to the present invention is to provide a measles vaccine virus genomic DNA consisting of the nucleotide sequence described below, with partial insertion mutational sequence or defective sequence.

A still further object of the invention is to provide an absolute identification method for a measles vaccine virus strain, which comprises detecting a specific nucleotide sequence consisting of the 15,894 nucleotides listed below coded by the genomic RNA of measles vaccine virus strain.

A yet still further object of the invention is to provide an absolute identification method comprising detecting a part of the nucleotide sequence of viral genomic DNA by the Northern blot technique and polymerase chain reaction method.

BRIEF DESCRIPTION OF THE DRAWINGS

The above and other objects and advantages according to the invention will be more readily apparent from a reading of the following detailed discussion taken with reference to the accompanying drawings, in which:

FIG. 3 is a genomic DNA sequence of the synthetic oligonucleotides (SEQ ID NOS:8–19) as complementary genome DNA.

DETAILED DISCUSSION

Figure 1:
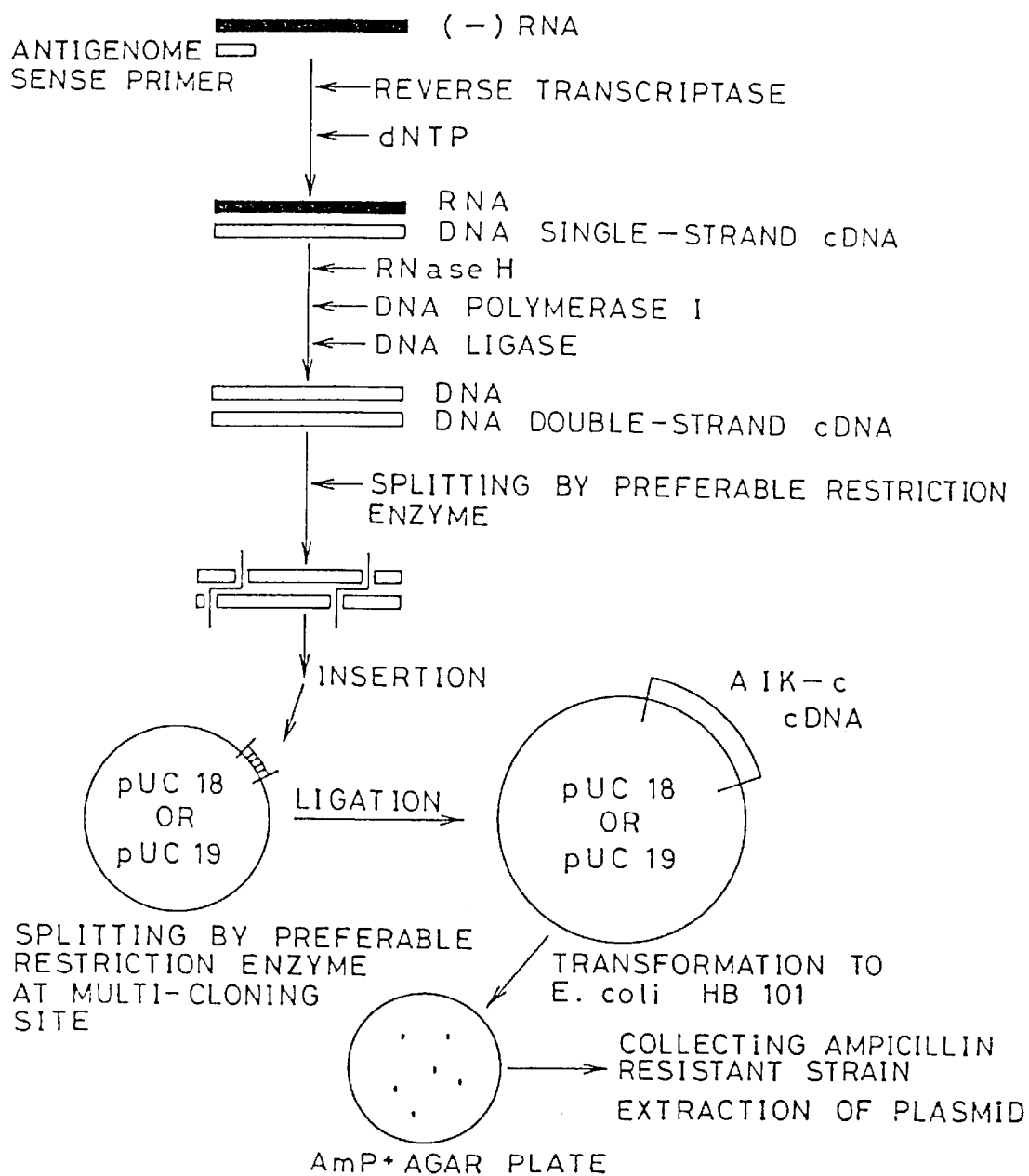
FIG. 1 is an outline of cDNA construction.
Figure 2:
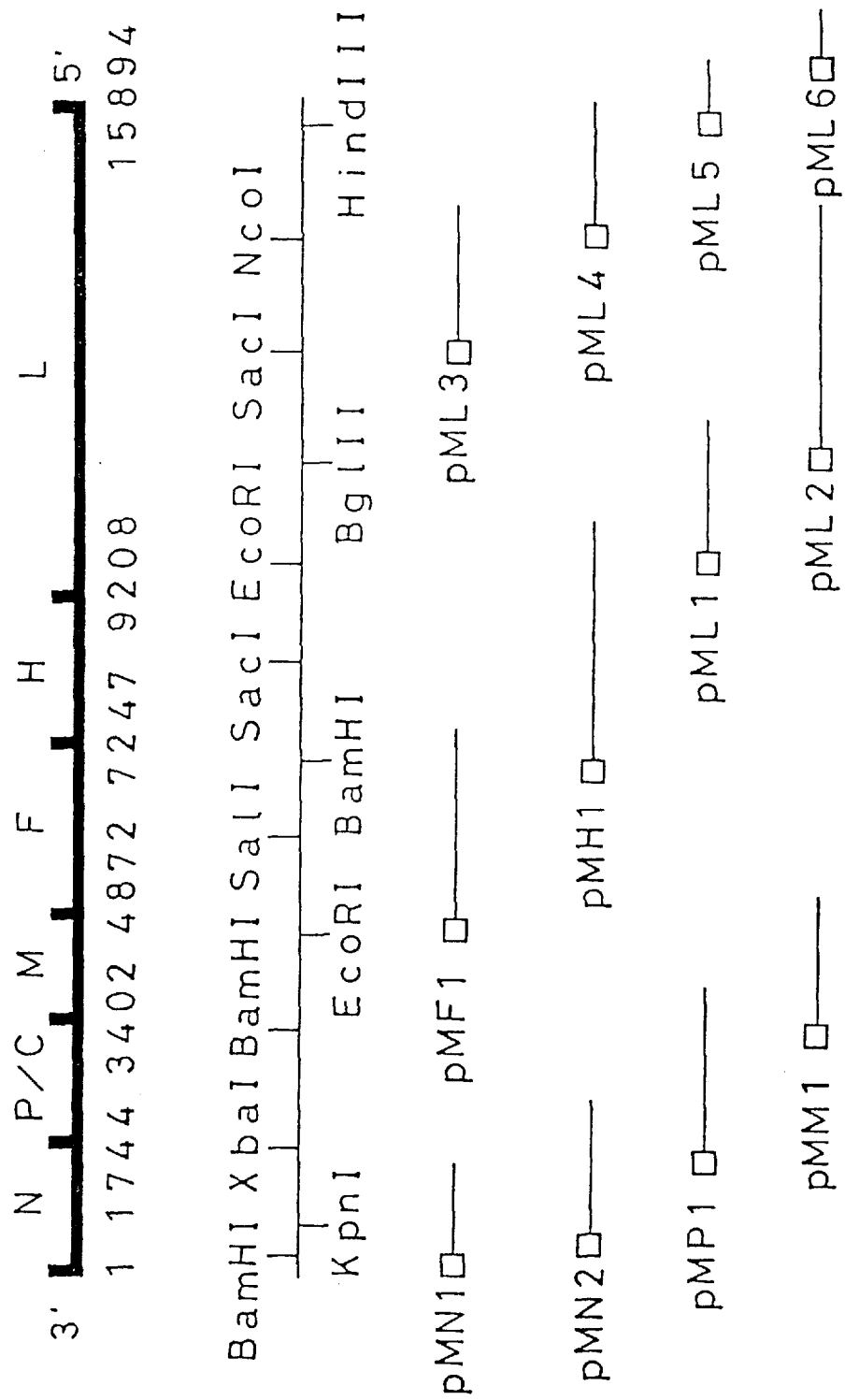
FIG. 2 is a mapping of cDNA clones of the AIK-C.

The inventors have determined that the complete cDNA sequence coded by the RNA genome of the AIK-C strain is as shown in SEQ ID NO:1. The coding regions of SEQ ID NO:1 encode the amino acid sequences of SEQ ID NOS:2–7.

The physical characteristics of the sequence are:

Sequence type: nucleic acid

Strandedness: single

Topology: linear

Molecule type: antigenomic DNA

Original source

Organism: attenuated measles vaccine

Strain: AIK-C

According to the present invention, a seed virus of the measles virus AIK-C strain is first used. This vaccine virus is propagated in chick embryo cells derived from specific pathogen-free hen's eggs to prepare so-called bulk vaccine, from which a virus suspension can be prepared by conventional purification techniques. The bulk vaccine can be a part of the virus pool prepared for commercial measles AIK-C strain vaccine.

The clarified virus suspension is purified by ultracentrifugation through continuous sucrose gradients. Virus RNA is extracted by the SDS-phenol method. Synthetic primer can be synthesized with approx. 25 mer synthetic primer by the amidide method.

The deoxyoligonucleotide, a synthetic primer, can be synthesized, for example, on a CYCLONE DNA SYNTHESIZER (Biosearch, Inc.)

The AIK-C virus genome RNA is used as a template for the synthesis of cDNA using the above synthetic oligonucleotide primer. The AIK-C virus genome RNA is reversely transcribed by reverse transcriptase to prepare single-strand cDNA, which is thereafter treated by the RNase H method to prepare double-strand cDNA. The double-stranded cDNAs are treated with appropriate restriction enzymes and are inserted into pUC plasmids (pUC 18 or pUC 19).

The above process is illustrated schematically in FIG. 1. *E. coli* K 12 strain HB101 is transformed with the resulting recombinant plasmid. The transformants are selected according to their ampicillin resistance. Colonies containing recombinant plasmids are screened by measuring the size of plasmic DNA by agarose gel electrophoresis. To determine the AIK-C genome sequence, the cDNA are subcloned into the bacteriophage M 13 series, and the single-strand M 13 phage DNAs are isolated from candidate subclones.

Determination of the obtained cDNA clone can be made using several restriction enzyme cleavage types. In the cDNA obtained using a synthetic primer such as MP-1, the restriction enzyme sites of BamHI, E coRV and Xbal are located. In the plasmid extracted from an ampicillin resistant strain, in case this type of cDNA is observed, approximately 1504 base fragments are identified by splitting with BamHI and Xbal in an agarose gel electrophoresis. Further treatment of these fragments with EcoRV provides two fragments of 650 and 854 base fragments.

Accordingly, an identification of the obtained cDNA clone is made by cleaving the inserted fragment in the plasmid and determining its size, or by determining the specific restriction site of measles DNA in the fragments.

To determine the base sequence, the cDNA, which are split by restriction enzymes to prepare cohesive ends or blunt ends, is inserted into M 13 phage vectors whose cloning parts are cleaved by the appropriate restriction enzymes. The phage containing the thus-prepared recombinant DNA is infected into *E. coli*. Single-strand recombinant DNA is extracted from the infected phage plaques, and the nucleotide sequence thereof is determined by the dideoxy chain termination method (dideoxy sequence method).

A primer such as pMN 2, the cDNA obtained from MP-1, is split by BamHI and Xbal, and is cloned with pUC plasmid. After determining the cDNA, the DNA fragment originated from AIK-C strain by splitting with the same restriction enzyme, further the fragment is split using EcoRV to prepare two fragments consisting of 650 bp and 854 bp.

These fragments are ligated into the M 13 replicative form double-strand DNA, which was previously split by BamHI and Xbal transfected into *E. coli*. After the recombinant phage is selected, the phage is infected in *E. coli* and allowed to multiply. Single-strand recombinant DNA is extracted from the supernatant phase of the phage solution and the nucleotide sequence thereof is determined by the dideoxy sequence method.

The viral genome of the AIK-C strain has been found to be constructed of 15,894 nucleotides and its entire sequence is shown in the sequence given above. A measles virus containing this RNA genome has the superior properties of AIK-C virus strain. The specific nucleotide sequence of AIK-C virus strain genome is determined by the PCR method and can be compared with the virus strain whether the strain is to be used for AIK-C strain virus vaccine or whether the prepared AIK-C strain virus vaccine is simply the maintaining properties of AIK-C strain. Furthermore, if an infant to whom the measles vaccine has been administered exhibits exanthema and antibodies against measles virus are observed in the lymphocyte of the infant, the causes thereof can be determined by comparing with the nucleotide sequence, as to whether the exanthema is caused by the administered vaccine or not.

The following examples are provided to illustrate the present invention but are not to be construed as limiting.

EXAMPLE 1

Determination of the nucleotide sequence of a virus obtained from AIK-C virus strain bulk vaccine Step a A seed virus of the AIK-C measles strain (Seed Lot 0-2) was inoculated up to an infectivity titer of 0.05 in chick embryo cells derived from specific pathogen-free hen's eggs cultured in a surface area cell culture (230 $cm^2$) in a large Roux bottle (approx. 1 liter volume). A culture medium (150 ml) of Eagle's minimum essential medium (MEM) containing 1% calf serum was added thereto and the virus was cultured at 33° C.

Step b

On the third day after inoculation, the cultured medium was removed, and then 150 ml of new medium was added and the cultivation was continued.

Step c

On the sixth day after inoculation of virus, the culture was removed. The layer of infected chick embryo cells was washed completely three times with 100 ml aliquots of Hank's solution. Cultivation was then continued at 33° C. after adding 200 ml of Eagle's MEM for cell culture, containing 0.1% sodium glutamate.

Step d

On the tenth day after virus seed inoculation, the specific cytopathogenic effect for measles virus was observed over the entire infected cell layer, and the culture medium was collected to produce the bulk vaccine solution (volume: approx. 200 ml, infectivity titer: $10^{7.2}$ $TCID_{50}$*/ml; *medium tissue culture infective dose).

Step e

The bulk vaccine solution was centrifuged at 3,000 rpm for 30 mins. and the supernatant solution removed therefrom was further centrifuged at 25,000 rpm for 90 mins. (Beckman. L 8-55M, rotor: SW 28)

Step f

After the further supernatant solution was removed, 1 ml of TEN buffer solution (10 mM-Tris HCl, 1 mM-EDTA, 100 mM-NaCl, pH 7.4) was added to the precipitate in each centrifuge tube, and the precipitate was well suspended therein to prepare concentrated virus. Each of the thus-obtained concentrated virus suspensions was adjusted to a final volume of 10 ml by adding TEN buffer solution, to prepare clarified virus suspension.

Step g

The clarified virus suspension (5 ml) was layered on 30–60% continuous sucrose gradients in two centrifuge tubes (Beckman centrifuge SW 41 rotor), each having 60% (w/v) sucrose solution in TEN buffer solution (6.8 ml) and 30% (w/v) sucrose solution in TEN buffer solution (6.8 ml) per tube, and centrifuged for 90 mins. at 207,000 g and 4° C. The suspension was fractionated and the fractions showing the highest infectivity titer ($10^{8.3}$ $TCID_{50}$/ml) were collected and again centrifuged by the same technique to prepare purified virus particles.

Step h

The purified virus particles were diluted five-fold with TEN buffer solution, and 200 μl of each was added into a respective 1.5 ml microtesttube, along with 5 μl of 20% SDS, 100 μl phenol and 100 μl chloroform, followed by complete stirring using a vortex mixer. The mixture was further centrifuged at 12,000 rpm for 5 mins. to separate the organic layer and the aqueous layer. The aqueous layer was collected into another 1.5 ml microtesttube and treated twice by phenol extraction (SDS-phenol extraction). The recovered aqueous layer was mixed with 5M-NaCl (1/25 volume), and ethanol (2.5 volume), allowed to stand at −20° C. for 2 hours, then centrifuged at 12,000 rpm for 10 mins. to collect precipitated RNA which was washed with 70% ethanol and dried. The dried material was dissolved in sterilized redistilled water (50 μl) and autoclaved to prepare an RNA suspension.

Step i

Cyclone DNA synthesizer

Synthetic primer deoxyoligonucleotide, 12 primers comprising approx. 25 mer of MP-1–MP-11 and BEP (dT)$_7$ as shown in FIG. 3 were synthesized using a Cyclone DNA Synthesizer sizer (Biosearch Inc., U.S.A.).

Step j

10 μl of the RNA suspension obtained in the above Step h (AIK-C virus genome RNA) was used as a template for the synthesis of DNA using 2 μl of the above synthetic oligonucleotide primers, MP-1 or MP-11, and cDNA was prepared by reverse transcriptase treatment. The cDNA was then transferred to double-strand cDNA by using RNase H-DNA polymerase I according to the technique described by Gubler and Hoffman in *GENE*, Vol. 25, pp. 263–269, (1983).

Step k

The obtained cDNA was cleaved at each of its restriction enzyme cleavage sites by BamHI-XbaI, XbaI-BamHI, BamHI-EcoRI, EcoRI-BamHI, BamHI-EcoRI, EcoRI, BglII, BglII-SacI and SacI-NcoI-XbaI. Each fragment was inserted into a corresponding cloning site of pUC plasmid (pUC 18 and pUC 19).

Step l

*E. coli* HB101 was transformed with the above recombinant plasmid to obtain ampicillin-resistant colonies. A plasmid DNA was extracted from the thus-obtained colonies, and the colonies containing recombinant plasmids were screened by measuring the size length of the plasmid DNA fragments by 0.8% agarose gel electrophoresis.

Step m

To obtain the 3' terminal clone of the AIK-C genome, poly(A) was tailed at the 3' end of the genomic RNA, an RNA suspension obtained in the above Step h, with poly(A) polymerase and adenosine triphosphate (ATP). The thus-obtained 3'A tailed RNA suspension, i.e. the polyadenylated RNA, was reversely transcribed using BEP(dT)$_7$ primer to prepare cDNA according to the above Step j. The BEP(dT)$_7$ primer has the sequence 5'-CTGTGAATTCTGC AGGATCCTTTTTTT-3' (SEQ ID NO:19).

Step n

The 5' terminal clone was synthesized with the primer located close to the 5' terminus. That is, the primer contained complementary DNA in a domain of 15,592–15,615 in the measles virus genome. The synthetic primer has the sequence 5'-TGGAAGCTTATCCAGAATCT CAAGTCCGGCT-3'(SEQ ID NO: 18).

A DNA-RNA hybrid was prepared by using the said synthetic DNA as a primer with reverse transcriptase. After alkaline treatment of the hybrid, poly(dA), i.e. dATP, was tailed to the 3' end of the resulting cDNA with terminal deoxynucleotidyl transferase. It was subsequently converted to the double-stranded cDNA using the BEP(dT)$_7$ primer in the above Step m and the Klenow fragment.

Step o

The thus-obtained cDNAs were subcloned into the bacteriophage M 13 series vector (mp 18 and mp 19), and the single-strand M 13 phage DNAs were isolated. The nucleotide sequence of those cDNAs was determined with the said single-stranded DNA by means of the dideoxy chain termination method using a 7-DEAZA-dGTP sequencing kit (Takara Shuzo).

Step p

Computer analysis of the nucleotide and peptide sequence was performed using GENETYX software.

EXAMPLE 2

Determination of the viral nucleotide of AIK-C strain seed virus grown in Vero cells (African green monkey live cells

Step a

AIK-C strain seed virus (Seed Lot No. 0-2) was inoculated in Vero cells previously cultured in a large size Roux bottle according to the method described in Example 1, and incubated at 33° C.

Step b

On the fifth day of incubation, the infected cell layers were washed with Hank's solution, then Eagle's MEM (200 ml) without calf serum was added thereto and the culture was further incubated for two days. The incubated viral culture was collected to obtain a bulk virus suspension (approx. 200 ml, infective titer: $10^{6.5}$ TCID$_{50}$/ml).

Step c

The bulk vaccine was centrifuged at 3,000 rpm for 30 mins., whereafter the supernatant suspension removed therefrom was centrifuged at 25,000 rpm for 90 mins. (Centrifuge: Beckman L8-55M, rotor: SW 28).

Step d

After the further supernatant solution was removed, 1 ml of TEN buffer solution (10 mM Tris-HCl, 1 mM EDTA, 100 mM NaCl, pH 7.4) was added to the precipitate in each centrifuge tube, and the precipitate was suspended completely to prepare concentrated virus material, which was adjusted to a volume of 10 ml by adding TEN buffer solution to prepare the starting material virus suspension.

Step e 5 ml of the virus suspension starting material was layered on a 30–60% continuous sucrose gradient in each of two tubes consisting of 60% (w/v) sucrose solution (TEN buffer solution) (6.8 ml) and 30% (w/v) sucrose solution (TEN buffer solution) (6.8 ml), then centrifuged at 207,000 g for 90 mins. at 4° C.

The centrifuged suspension in each tube was fractionated by means of a fraction collector and fractions showing high infectivity ($10^{8.3}$ TCID$_{50}$/ml) were collected. The collected fractions were again centrifuged in the same manner to recover purified virus.

Step f

200 µl of the purified virus, diluted five-fold with TEN buffer solution, was added to each of a series of 1.5 ml microtesttubes. To each tube was then added 5 µl of 20% SDS, 100 µl of phenol and 100 µl chloroform, and the contents of the tubes were completely stirred using a vortex mixer. The organic layer and aqueous layer were separated by centrifuging at 12,000 rpm for 5 mins. The aqueous layer was collected in another 1.5 ml microtesttube, and extracted twice with the same SDS-phenol extractant as above.

The recovered aqueous layer was mixed with 5M NaCl (1/25 volume) and ethanol (2.5 volume), allowed to stand at −20° C. for 2 hours, and centrifuged at 12,000 rpm for 10 mins. to collect precipitated RNA. The precipitated RNA was then washed with 70% ethanol, and dried. An RNA suspension was prepared with sterilization of the dried material and dissolved in redistilled water (50 µl).

Step g

Cyclone DNA Synthesizer

Synthetic primer deoxyoligonucleotide, 12 primers, comprising approx. 25 mer of MP-1–MP-11 and BEP(dT)$_7$ as shown in FIG. 3 were synthesized using a cyclone DNA synthesizer (Biosearch Inc., U.S.A.).

Step h

The RNA suspension (10 μl) obtained in the above Example 1 (AIK-C virus genome RNA) was used as a template for the synthesis of cDNA using synthetic oligonucleotide primers (the above synthetic DNA, 2 μl of synthetic primer, MP-1 or MP-11) and cDNA was prepared by reverse transcriptase treatment. The cDNA was then transferred to double-strand cDNA using RNaseH-DNA polymerase I according to the method of Gubler and Hoffman cited above.

Step i

The obtained cDNA was cleaved at each of its restriction enzyme cleavage sites by BamHI-Xbal, Xbal-BamHI, BamHI-EcoRI, EcoRI-BamHI, BamHI-EcoRI, EcoRI-BglII, BglII-SacI and SacI-NcoI-Xbal. Each fragment was inserted into a corresponding cloning site of pUC plasmid (pUC 18 and pUC 19).

Step j

*E. coli* HB101 was transformed with the above recombinant plasmid to obtain ampicillin-resistant colonies. A plasmid DNA was extracted from the thus-obtained colonies, and the colonies containing recombinant plasmids were screened by measuring the size length of plasmid DNA fragments by 0.8% agarose gel electrophoresis.

Step k

To obtain the 3' terminal clone of the AIK-C genome, poly(A) was tailed at the 3' end of the genomic RNA, an RNA suspension obtained in the above Step f, with poly(A) polymerase and adenosine triphosphate (ATP). The thus-obtained 3' tailed RNA suspension, i.e. the polyadenylated RNA, was reversely transcribed using BEP$(dT)_7$ primer to prepare cDNA according to the above Step h. The BEP$(dT)_7$ primer has the sequence 5'-CTGTGAATTCTGCAG GATCCTTTTTTT-3' (SEQ ID NO:18).

Step l

The 5' terminal clone was synthesized with the primer located close to the 5' terminals. That is, the primer contained complementary DNA in a domain of 15,592–15,615 in the measles virus genome. The synthetic primer has the sequence 5'-TGGAAGCTTATCCAGAATCTCAA GTCCGGCT-3' (SEQ ID NO:18).

A DNA-RNA hybrid was prepared by using the said synthetic DNA as a primer with reverse transcriptase. After alkaline treatment of the hybrid, poly(Da), i.e. dATP, was tailed to the 3' end of the resulting cDNA with terminal deoxynucleotidyl transferase. It was subsequently converted to the double-stranded cDNA using the BEP$(dT)_7$ primer in the above Step k and the Klenow fragment.

Step m

The thus-obtained cDNA were subcloned into the bacteriophage M 13 series vector (mp 18 and mp 19), and the single-stranded M 13 phage DNAs were isolated. The nucleotide sequence of those cDNAs was determined with the said single-stranded DNA by means of the dideoxy chain termination method using a 7-DEAZA-dGTP sequencing kit (Takara Shuzo).

Step n

Computer analysis of the nucleotide and peptide sequences was performed using GENETYX software.

EXAMPLE 3

Identification by the PCR method of measles virus obtained from a patient on the first day when measles symptoms appeared Step a A blood specimen (approx. 5 ml) was collected from a patient on his first day displaying measles exanthema. Lymphocytes were separated using Ficoll (trade name).

Step b

The lymphocytes were washed twice with PBS. 200 μl of a denaturation solution D (4M guanidium thiocyanate, 25 mM sodium citrate, pH 7.5; 0.5% sarcosine, 0.1M 2-mercapto ethanol) was added thereto. After gentle stirring, 2M sodium acetate (20 μl, pH 4), phenol (200 μl) and chloroform (100 μl), were added in that order.

The mixture was treated with a vortex mixer for 10 sec. and allowed to stand in ice water for 15 mins. Then the mixture was centrifuged at 10,000 g for 20 mins. to recover an aqueous layer. An equal volume of isopropanol was added thereto, and the mixture was allowed to stand at −20° C. for one hour, then centrifuged at 10,000 g for 20 mins. to precipitate RNA. This procedure was performed according to the technique described by Chomoczynski and Sacchi in *Anal. Biochem.*, Vol. 162, pp. 156–159 (1987).

Step c

The thus-obtained RNA was subjected to a reverse transcriptase reaction and the PCR method.

Step d

Nucleotide sequencing and identification of the measles virus AIK-C vaccine strain and the naturally-occurring strain performed.

Although the present invention has been described in connection with various preferred embodiments thereof, it will be appreciated that these embodiments are provided solely for purposes of illustration, and should not be construed as limiting the scope of the invention. Other embodiments and applications of the invention will be readily apparent to those skilled in the art from reading the present specification and practicing the techniques described herein, without departing whatsoever from the scope and spirit of the appended claims.

What is claimed is:

1. Purified and isolated amino acid sequences consisting of SEQ ID NOS:2–7.

2. Purified and isolated amino acid sequence consisting of SEQ ID NO:2.

3. Purified and isolated amino acid sequence consisting of SEQ ID NO:3.

4. Purified and isolated amino acid sequence consisting of SEQ ID NO:4.

5. Purified and isolated amino acid sequence consisting of SEQ ID NO:5.

6. Purified and isolated amino acid sequence consisting of SEQ ID NO:6.

7. Purified and isolated amino acid sequence consisting of SEQ ID NO:7.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 15894 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 108..1682

( i x ) FEATURE:
        ( A ) NAME/KEY: CDS
        ( B ) LOCATION: 1807..3327

( i x ) FEATURE:
        ( A ) NAME/KEY: CDS
        ( B ) LOCATION: 3438..4442

( i x ) FEATURE:
        ( A ) NAME/KEY: CDS
        ( B ) LOCATION: 5458..7107

( i x ) FEATURE:
        ( A ) NAME/KEY: CDS
        ( B ) LOCATION: 7271..9121

( i x ) FEATURE:
        ( A ) NAME/KEY: CDS
        ( B ) LOCATION: 9234..15782

( x i ) SEQUENCE DESCRIPTION: SEQ ID NO:1:

```
ACCAAACAAA GTTGGGTAAG GATAGTTCAA TCAATGATCA TCTTCTAGTG CACTTAGGAT            60

TCAAGATCCT ATTATCAGGG ACAAGAGCAG GATTAGGGAT ATCCGAG ATG GCC ACA            116
                                                     Met Ala Thr
                                                       1

CTT TTA AGG AGC TTA GCA TTG TTC AAA AGA AAC AAG GAC AAA CCA CCC            164
Leu Leu Arg Ser Leu Ala Leu Phe Lys Arg Asn Lys Asp Lys Pro Pro
        5                  10                  15

ATT ACA TCA GGA TCC GGT GGA GCC ATC AGA GGA ATC AAA CAC ATT ATT            212
Ile Thr Ser Gly Ser Gly Gly Ala Ile Arg Gly Ile Lys His Ile Ile
 20                  25                  30                  35

ATA GTA CCA ATC CCT GGA GAT TCC TCA ATT ACC ACT CGA TCC AGA CTT            260
Ile Val Pro Ile Pro Gly Asp Ser Ser Ile Thr Thr Arg Ser Arg Leu
                40                  45                  50
```

| | | | | | | | | | | | | | | | | |
|---|---|---|---|---|---|---|---|---|---|---|---|---|---|---|---|---|
| CTG | GAC | CGG | TTG | GTC | AGG | TTA | ATT | GGA | AAC | CCG | GAT | GTG | AGC | GGG | CCC | 308 |
| Leu | Asp | Arg | Leu | Val | Arg | Leu | Ile | Gly | Asn | Pro | Asp | Val | Ser | Gly | Pro | |
| | | | 55 | | | | 60 | | | | | 65 | | | | |
| AAA | CTA | ACA | GGG | GCA | CTA | ATA | GGT | ATA | TTA | TCC | TTA | TTT | GTG | GAG | TCT | 356 |
| Lys | Leu | Thr | Gly | Ala | Leu | Ile | Gly | Ile | Leu | Ser | Leu | Phe | Val | Glu | Ser | |
| | | 70 | | | | 75 | | | | | 80 | | | | | |
| CCA | GGT | CAA | TTG | ATT | CAG | AGG | ATC | ACC | GAT | GAC | CCT | GAC | GTT | AGC | ATA | 404 |
| Pro | Gly | Gln | Leu | Ile | Gln | Arg | Ile | Thr | Asp | Asp | Pro | Asp | Val | Ser | Ile | |
| | 85 | | | | 90 | | | | | 95 | | | | | | |
| AGG | CTG | TTA | GAG | GTT | GTC | CAG | AGT | GAC | CAG | TCA | CAA | TCT | GGC | CTT | ACC | 452 |
| Arg | Leu | Leu | Glu | Val | Val | Gln | Ser | Asp | Gln | Ser | Gln | Ser | Gly | Leu | Thr | |
| 100 | | | | | 105 | | | | | 110 | | | | | 115 | |
| TTC | GCA | TCA | AGA | GGT | ACC | AAC | ATG | GAG | GAT | GAG | GCG | GAC | AAA | TAC | TTT | 500 |
| Phe | Ala | Ser | Arg | Gly | Thr | Asn | Met | Glu | Asp | Glu | Ala | Asp | Lys | Tyr | Phe | |
| | | | | 120 | | | | | 125 | | | | | 130 | | |
| TCA | CAT | GAT | GAT | CCA | ATT | AGT | AGT | GAT | CAA | TCC | AGG | TTC | GGA | TGG | TTC | 548 |
| Ser | His | Asp | Asp | Pro | Ile | Ser | Ser | Asp | Gln | Ser | Arg | Phe | Gly | Trp | Phe | |
| | | | 135 | | | | | 140 | | | | | 145 | | | |
| GAG | AAC | AAG | GAA | ATC | TCA | GAT | ATT | GAA | GTG | CAA | GAC | CCT | GAG | GGA | TTC | 596 |
| Glu | Asn | Lys | Glu | Ile | Ser | Asp | Ile | Glu | Val | Gln | Asp | Pro | Glu | Gly | Phe | |
| | | 150 | | | | | 155 | | | | | 160 | | | | |
| AAC | ATG | ATT | CTG | GGT | ACC | ATC | CTA | GCC | CAA | ATT | TGG | GTC | TTG | CTC | GCA | 644 |
| Asn | Met | Ile | Leu | Gly | Thr | Ile | Leu | Ala | Gln | Ile | Trp | Val | Leu | Leu | Ala | |
| | 165 | | | | | 170 | | | | | 175 | | | | | |
| AAG | GCG | GTT | ACG | GCC | CCA | GAC | ACG | GCA | GCT | GAT | TCG | GAG | CTA | AGA | AGG | 692 |
| Lys | Ala | Val | Thr | Ala | Pro | Asp | Thr | Ala | Ala | Asp | Ser | Glu | Leu | Arg | Arg | |
| 180 | | | | | 185 | | | | | 190 | | | | | 195 | |
| TGG | ATA | AAG | TAC | ACC | CAA | CAA | AGA | AGG | GTA | GTT | GGT | GAA | TTT | AGA | TTG | 740 |
| Trp | Ile | Lys | Tyr | Thr | Gln | Gln | Arg | Arg | Val | Val | Gly | Glu | Phe | Arg | Leu | |
| | | | | 200 | | | | | 205 | | | | | 210 | | |
| GAG | AGA | AAA | TGG | TTG | GAT | GTG | GTG | AGG | AAC | AGG | ATT | GCC | GAG | GAC | CTC | 788 |
| Glu | Arg | Lys | Trp | Leu | Asp | Val | Val | Arg | Asn | Arg | Ile | Ala | Glu | Asp | Leu | |
| | | | 215 | | | | | 220 | | | | | 225 | | | |
| TCC | TTA | CGC | CGA | TTC | ATG | GTC | GCT | CTA | ATC | CTG | GAT | ATC | AAG | AGA | ACA | 836 |
| Ser | Leu | Arg | Arg | Phe | Met | Val | Ala | Leu | Ile | Leu | Asp | Ile | Lys | Arg | Thr | |
| | | 230 | | | | | 235 | | | | | 240 | | | | |
| CCC | GGA | AAC | AAA | CCC | AGG | ATT | GCT | GAA | ATG | ATA | TGT | GAC | ATT | GAT | ACA | 884 |
| Pro | Gly | Asn | Lys | Pro | Arg | Ile | Ala | Glu | Met | Ile | Cys | Asp | Ile | Asp | Thr | |
| | 245 | | | | | 250 | | | | | 255 | | | | | |
| TAT | ATC | GTA | GAG | GCA | GGA | TTA | GCC | AGT | TTT | ATC | CTG | ACT | ATT | AAG | TTT | 932 |
| Tyr | Ile | Val | Glu | Ala | Gly | Leu | Ala | Ser | Phe | Ile | Leu | Thr | Ile | Lys | Phe | |
| 260 | | | | | 265 | | | | | 270 | | | | | 275 | |
| GGG | ATA | GAA | ACT | ATG | TAT | CCT | GCT | CTT | GGA | CTG | CAT | GAA | TTT | GCT | GGT | 980 |
| Gly | Ile | Glu | Thr | Met | Tyr | Pro | Ala | Leu | Gly | Leu | His | Glu | Phe | Ala | Gly | |
| | | | | 280 | | | | | 285 | | | | | 290 | | |
| GAG | TTA | TCC | ACA | CTT | GAG | TCC | TTG | ATG | AAC | CTT | TAC | CAG | CAA | ATG | GGG | 1028 |
| Glu | Leu | Ser | Thr | Leu | Glu | Ser | Leu | Met | Asn | Leu | Tyr | Gln | Gln | Met | Gly | |
| | | | 295 | | | | | 300 | | | | | 305 | | | |
| GAA | ACT | GCA | CCC | TAC | ATG | GTA | AAC | CTG | GAG | AAC | TCA | ATT | CAG | AAC | AAG | 1076 |
| Glu | Thr | Ala | Pro | Tyr | Met | Val | Asn | Leu | Glu | Asn | Ser | Ile | Gln | Asn | Lys | |
| | | 310 | | | | | 315 | | | | | 320 | | | | |
| TTC | AGT | GCA | GGA | TCA | TAC | CCT | CTG | CTC | TGG | AGC | TAT | GCC | ATG | GGA | GTA | 1124 |
| Phe | Ser | Ala | Gly | Ser | Tyr | Pro | Leu | Leu | Trp | Ser | Tyr | Ala | Met | Gly | Val | |
| | 325 | | | | | 330 | | | | | 335 | | | | | |
| GGA | GTG | GAA | CTT | GAA | AAC | TCC | ATG | GGA | GGT | TTG | AAC | TTT | GGC | CGA | TCT | 1172 |
| Gly | Val | Glu | Leu | Glu | Asn | Ser | Met | Gly | Gly | Leu | Asn | Phe | Gly | Arg | Ser | |
| 340 | | | | | 345 | | | | | 350 | | | | | 355 | |
| TAC | TTT | GAT | CCA | GCA | TAT | TTT | AGA | TTA | GGG | CAA | GAG | ATG | GTA | AGG | AGG | 1220 |
| Tyr | Phe | Asp | Pro | Ala | Tyr | Phe | Arg | Leu | Gly | Gln | Glu | Met | Val | Arg | Arg | |
| | | | | 360 | | | | | 365 | | | | | 370 | | |

-continued

| | | | | | | | | | | | | | | | | |
|---|---|---|---|---|---|---|---|---|---|---|---|---|---|---|---|---|
| TCA | GCT | GGA | AAG | GTC | AGT | TCC | ACA | TTG | GCA | TCT | GAA | CTC | GGT | ATC | ACT | 1268 |
| Ser | Ala | Gly | Lys 375 | Val | Ser | Ser | Thr 380 | Leu | Ala | Ser | Glu | Leu 385 | Gly | Ile | Thr | |
| GCC | GAG | GAT | GCA | AGG | CTT | GTT | TCA | GAG | ATT | GCA | ATG | CAT | ACT | ACT | GAG | 1316 |
| Ala | Glu | Asp 390 | Ala | Arg | Leu | Val | Ser 395 | Glu | Ile | Ala | Met | His 400 | Thr | Thr | Glu | |
| GAC | AAG | ATC | AGT | AGA | GCG | GTT | GGA | CCC | AGA | CAA | GCC | CAA | GTA | TCA | TTT | 1364 |
| Asp | Lys 405 | Ile | Ser | Arg | Ala | Val 410 | Gly | Pro | Arg | Gln | Ala 415 | Gln | Val | Ser | Phe | |
| CTA | CAC | GGT | GAT | CAA | AGT | GAG | AAT | GAG | CTA | CCG | AGA | TTG | GGG | GGC | AAG | 1412 |
| Leu 420 | His | Gly | Asp | Gln | Ser 425 | Glu | Asn | Glu | Leu | Pro 430 | Arg | Leu | Gly | Gly | Lys 435 | |
| GAA | GAT | AGG | AGG | GTC | AAA | CAG | AGT | CGA | GGA | GAA | GCC | AGG | GAG | AGC | TAC | 1460 |
| Glu | Asp | Arg | Arg | Val 440 | Lys | Gln | Ser | Arg | Gly 445 | Glu | Ala | Arg | Glu | Ser 450 | Tyr | |
| AGA | GAA | ACC | GGG | CCC | AGC | AGA | GCA | AGT | GAT | GCG | AGA | GCT | GCC | CAT | CTT | 1508 |
| Arg | Glu | Thr | Gly 455 | Pro | Ser | Arg | Ala | Ser 460 | Asp | Ala | Arg | Ala | Ala 465 | His | Leu | |
| CCA | ACC | GGC | ACA | CCC | CTA | GAC | ATT | GAC | ACT | GCA | TCG | GAG | TCC | AGC | CAA | 1556 |
| Pro | Thr | Gly 470 | Thr | Pro | Leu | Asp | Ile 475 | Asp | Thr | Ala | Ser | Glu 480 | Ser | Ser | Gln | |
| GAT | CCG | CAG | GAC | AGT | CGA | AGG | TCA | GCT | GAC | GCC | CTG | CTT | AGG | CTG | CAA | 1604 |
| Asp | Pro 485 | Gln | Asp | Ser | Arg | Arg 490 | Ser | Ala | Asp | Ala | Leu 495 | Leu | Arg | Leu | Gln | |
| GCC | ATG | GCA | GGA | ATC | TCG | GAA | GAA | CAA | GGC | TCA | GAC | ACG | GAC | ACC | CCT | 1652 |
| Ala | Met | Ala | Gly | Ile 505 | Ser | Glu | Glu | Gln | Gly 510 | Ser | Asp | Thr | Asp | Thr | Pro 515 | |
| Ala 500 | | | | | | | | | | | | | | | | |
| ATA | GTG | TAC | AAT | GAC | AGA | AAT | CTT | CTA | GAC | TAGGTGCGAG | | AGGCCGAGGA | | | | 1702 |
| Ile | Val | Tyr | Asn | Asp 520 | Arg | Asn | Leu | Leu | Asp 525 | | | | | | | |

CCAGAACAAC ATCCGCCTAC CCTCCATCAT TGTTATAAAA AACTTAGGAA CCAGGTCCAC    1762

ACAGCCGCCA GCCCATCAAC CATCCACTCC CACGATTGGA GCCG ATG GCA GAA GAG    1818
                           Met Ala Glu Glu
                            1

| | | | | | | | | | | | | | | | | |
|---|---|---|---|---|---|---|---|---|---|---|---|---|---|---|---|---|
| CAG | GCA | CGC | CAT | GTC | AAA | AAC | GGA | CTG | GAA | TGC | ATC | CGG | GCT | CTC | AAG | 1866 |
| Gln | Ala | Arg | His | Val 10 | Lys | Asn | Gly | Leu | Glu 15 | Cys | Ile | Arg | Ala | Leu 20 | Lys | |
| 5 | | | | | | | | | | | | | | | | |
| GCC | GAG | CCC | ATC | GGC | TCA | CTG | GCC | ATC | GAG | GAA | GCT | ATG | GCA | GCA | TGG | 1914 |
| Ala | Glu | Pro | Ile | Gly 25 | Ser | Leu | Ala | Ile | Glu 30 | Glu | Ala | Met | Ala | Ala 35 | Trp | |
| TCA | GAA | ATA | TCA | GAC | AAC | CCA | GGA | CAG | GAG | CGA | GCC | ACC | TGC | AGG | GAA | 1962 |
| Ser | Glu | Ile | Ser 40 | Asp | Asn | Pro | Gly | Gln 45 | Glu | Arg | Ala | Thr | Cys 50 | Arg | Glu | |
| GAG | AAG | GCA | GGC | AGT | TCG | GGT | CTC | AGC | AAA | CCA | TGC | CTC | TCA | GCA | ATT | 2010 |
| Glu | Lys | Ala 55 | Gly | Ser | Ser | Gly | Leu 60 | Ser | Lys | Pro | Cys | Leu 65 | Ser | Ala | Ile | |
| GGA | TCA | ACT | GAA | GGC | GGT | GCA | CCT | CGC | ATC | CGC | GGT | CAG | GGA | CCT | GGA | 2058 |
| Gly | Ser | Thr 70 | Glu | Gly | Gly | Ala | Pro 75 | Arg | Ile | Arg | Gly | Gln 80 | Gly | Pro | Gly | |
| GAG | AGC | GAT | GAC | GAC | GCT | GAA | ACT | TTG | GGA | ATC | CCC | CCA | AGA | AAT | CTC | 2106 |
| Glu | Ser | Asp | Asp 85 | Asp | Ala | Glu | Thr | Leu 90 | Gly | Ile | Pro | Pro | Arg 95 | Asn | Leu 100 | |
| CAG | GCA | TCA | AGC | ACT | GGG | TTA | CAG | TGT | TAT | TAT | GTT | TAT | GAT | CAC | AGC | 2154 |
| Gln | Ala | Ser | Ser | Thr 105 | Gly | Leu | Gln | Cys | Tyr 110 | Tyr | Val | Tyr | Asp | His 115 | Ser | |
| GGT | GAA | GCG | GTT | AAG | GGA | ATC | CAA | GAT | GCT | GAC | TCT | ATC | ATG | GTT | CAA | 2202 |
| Gly | Glu | Ala | Val | Lys 120 | Gly | Ile | Gln | Asp | Ala 125 | Asp | Ser | Ile | Met | Val 130 | Gln | |
| TCA | GGC | CTT | GAT | GGT | GAT | AGC | ACC | CTA | TCA | GGA | GGA | GAC | AAT | GAA | TCT | 2250 |
| Ser | Gly | Leu | Asp | Gly | Asp | Ser | Thr | Leu | Ser | Gly | Gly | Asp | Asn | Glu | Ser | |

```
                    135                          140                              145
GAA  AAC  AGC  GAT  GTG  GAT  ATT  GGC  GAA  CCT  GAT  ACC  GAG  GGA  TAT  GCT       2298
Glu  Asn  Ser  Asp  Val  Asp  Ile  Gly  Glu  Pro  Asp  Thr  Glu  Gly  Tyr  Ala
     150                      155                      160

ATC  ACT  GAC  CGG  GGA  TCT  GCT  CCC  ATC  TCT  ATG  GGG  TTC  AGG  GCT  TCT       2346
Ile  Thr  Asp  Arg  Gly  Ser  Ala  Pro  Ile  Ser  Met  Gly  Phe  Arg  Ala  Ser
165                      170                      175                      180

GAT  GTT  GAA  ACT  GCA  GAA  GGA  GGG  GAG  ATC  CAC  GAG  CTC  CTG  AGA  CTC       2394
Asp  Val  Glu  Thr  Ala  Glu  Gly  Gly  Glu  Ile  His  Glu  Leu  Leu  Arg  Leu
                         185                      190                      195

CAA  TCC  AGA  GGC  AAC  AAC  TTT  CCG  AAG  CTT  GGG  AAA  ACT  CTC  AAT  GTT       2442
Gln  Ser  Arg  Gly  Asn  Asn  Phe  Pro  Lys  Leu  Gly  Lys  Thr  Leu  Asn  Val
               200                      205                      210

CCT  CCG  CCC  CCG  GAC  CCC  GGT  AGG  GCC  AGC  ACT  TCC  GGG  ACA  CCC  ATT       2490
Pro  Pro  Pro  Pro  Asp  Pro  Gly  Arg  Ala  Ser  Thr  Ser  Gly  Thr  Pro  Ile
          215                      220                      225

AAA  AAG  GGC  ACA  GAG  CGC  AGA  TTA  GCC  TCA  TTT  GGA  ACG  GAG  ATC  GCG       2538
Lys  Lys  Gly  Thr  Glu  Arg  Arg  Leu  Ala  Ser  Phe  Gly  Thr  Glu  Ile  Ala
     230                      235                      240

TCT  TTA  TTG  ACA  GGT  GGT  GCA  ACC  CAA  TGT  GCT  CGA  AAG  TCA  CCC  TCG       2586
Ser  Leu  Leu  Thr  Gly  Gly  Ala  Thr  Gln  Cys  Ala  Arg  Lys  Ser  Pro  Ser
245                      250                      255                      260

GAA  CCA  TCA  GGG  CCA  GGT  GCA  CCT  GCG  GGG  AAT  GTC  CCC  GAG  TAT  GTG       2634
Glu  Pro  Ser  Gly  Pro  Gly  Ala  Pro  Ala  Gly  Asn  Val  Pro  Glu  Tyr  Val
                         265                      270                      275

AGC  AAT  GCC  GCA  CTG  ATA  CAG  GAG  TGG  ACA  CCC  GAA  TCT  GGT  ACC  ACA       2682
Ser  Asn  Ala  Ala  Leu  Ile  Gln  Glu  Trp  Thr  Pro  Glu  Ser  Gly  Thr  Thr
               280                      285                      290

ATC  TCC  CCG  AGA  TCC  CAG  AAT  AAT  GAA  GAA  GGG  GGA  GAC  TAT  TAT  GAT       2730
Ile  Ser  Pro  Arg  Ser  Gln  Asn  Asn  Glu  Glu  Gly  Gly  Asp  Tyr  Tyr  Asp
          295                      300                      305

GAT  GAG  CTG  TTC  TCT  GAT  GTC  CAA  GAT  ATT  AAA  ACA  GCC  TTG  GCC  AAA       2778
Asp  Glu  Leu  Phe  Ser  Asp  Val  Gln  Asp  Ile  Lys  Thr  Ala  Leu  Ala  Lys
     310                      315                      320

ATA  CAC  GAG  GAT  AAT  CAG  AAG  ATA  ATC  TCC  AAG  CTA  GAA  TCA  CTG  CTG       2826
Ile  His  Glu  Asp  Asn  Gln  Lys  Ile  Ile  Ser  Lys  Leu  Glu  Ser  Leu  Leu
325                      330                      335                      340

TTA  TTG  AAG  GGA  GAA  GTT  GAG  TCA  ATT  AAG  AAG  CAG  ATC  AAC  AGG  CAA       2874
Leu  Leu  Lys  Gly  Glu  Val  Glu  Ser  Ile  Lys  Lys  Gln  Ile  Asn  Arg  Gln
                         345                      350                      355

AAT  ATC  AGC  ATA  TCC  ACC  CTG  GAA  GGA  CAC  CTC  TCA  AGC  ATC  ATG  ATC       2922
Asn  Ile  Ser  Ile  Ser  Thr  Leu  Glu  Gly  His  Leu  Ser  Ser  Ile  Met  Ile
               360                      365                      370

GCC  ATT  CCT  GGA  CTT  GGG  AAG  GAT  CCC  AAC  GAC  CCC  ACT  GCA  GAT  GTC       2970
Ala  Ile  Pro  Gly  Leu  Gly  Lys  Asp  Pro  Asn  Asp  Pro  Thr  Ala  Asp  Val
          375                      380                      385

GAA  ATC  AAT  CCC  GAC  TTG  AAA  CCC  ATC  ATA  GGC  AGA  GAT  TCA  GGC  CGA       3018
Glu  Ile  Asn  Pro  Asp  Leu  Lys  Pro  Ile  Ile  Gly  Arg  Asp  Ser  Gly  Arg
     390                      395                      400

GCA  CTG  GCC  GAA  GTT  CTC  AAG  AAA  CCC  GTT  GCC  AGC  CGA  CAA  CTC  CAA       3066
Ala  Leu  Ala  Glu  Val  Leu  Lys  Lys  Pro  Val  Ala  Ser  Arg  Gln  Leu  Gln
405                      410                      415                      420

GGA  ATG  ACA  AAT  GGA  CGG  ACC  AGT  TCC  AGA  GGA  CAG  CTG  CTG  AAG  GAA       3114
Gly  Met  Thr  Asn  Gly  Arg  Thr  Ser  Ser  Arg  Gly  Gln  Leu  Leu  Lys  Glu
                         425                      430                      435

TTT  CAG  CCA  AAG  CCG  ATC  GGG  AAA  AAG  ATG  AGC  TCA  GCC  GTC  GGG  TTT       3162
Phe  Gln  Pro  Lys  Pro  Ile  Gly  Lys  Lys  Met  Ser  Ser  Ala  Val  Gly  Phe
               440                      445                      450

GTT  CCT  GAC  ACC  GGC  CCT  GCA  TCA  CGC  AGT  GTA  ATC  CGC  TCC  ATT  ATA       3210
Val  Pro  Asp  Thr  Gly  Pro  Ala  Ser  Arg  Ser  Val  Ile  Arg  Ser  Ile  Ile
```

-continued

|     | 455 |     |     |     | 460 |     |     |     |     | 465 |     |     |     |     |      |
|-----|-----|-----|-----|-----|-----|-----|-----|-----|-----|-----|-----|-----|-----|-----|------|
| AAA | TCC | AGC | CGG | CTA | GAG | GAG | GAT | CGG | AAG | CGT | TAC | CTG | ATG | ACT | CTC  | 3258 |
| Lys | Ser | Ser | Arg | Leu | Glu | Glu | Asp | Arg | Lys | Arg | Tyr | Leu | Met | Thr | Leu  |
|     | 470 |     |     |     | 475 |     |     |     |     | 480 |     |     |     |     |      |

| CTT | GAT | GAT | ATC | AAA | GGA | GCC | AAT | GAT | CTT | GCC | AAG | TTC | CAC | CAG | ATG  | 3306 |
| Leu | Asp | Asp | Ile | Lys | Gly | Ala | Asn | Asp | Leu | Ala | Lys | Phe | His | Gln | Met  |
| 485 |     |     |     |     | 490 |     |     |     |     | 495 |     |     |     |     | 500  |

| CTG | ATG | AAG | ATA | ATA | ATG | AAG | TAGCTACAGC | TCAACTTACC | TGCCAACCCC | 3357 |
| Leu | Met | Lys | Ile | Ile | Met | Lys |            |            |            |
|     |     |     |     | 505 |     |     |            |            |            |

ATGCCAGTCG ACCCAACTAG TACAACCTAA ATCCATTATA AAAAACTTAG GAGCAAAGTG 3417

| ATTGCCTCCC AAGTTCCACA ATG | ACA | GAG | ATC | TAC | GAC | TTC | GAC | AAG | TCG | 3467 |
|                           | Met | Thr | Glu | Ile | Tyr | Asp | Phe | Asp | Lys | Ser |
|                           |  1  |     |     |     |  5  |     |     |     |     | 10  |

| GCA | TGG | GAC | ATC | AAA | GGG | TCG | ATC | GCT | CCG | ATA | CAA | CCC | ACC | ACC | TAC | 3515 |
| Ala | Trp | Asp | Ile | Lys | Gly | Ser | Ile | Ala | Pro | Ile | Gln | Pro | Thr | Thr | Tyr |
|     |     |     |     | 15  |     |     |     |     | 20  |     |     |     |     | 25  |     |

| AGT | GAT | GGC | AGG | CTG | GTG | CCC | CAG | GTC | AGA | GTC | ATA | GAT | CCT | GGT | CTA | 3563 |
| Ser | Asp | Gly | Arg | Leu | Val | Pro | Gln | Val | Arg | Val | Ile | Asp | Pro | Gly | Leu |
|     |     |     | 30  |     |     |     |     | 35  |     |     |     |     | 40  |     |     |

| GGC | GAC | AGG | AAG | GAT | GAA | TGC | TTT | ATG | TAC | ATG | TCT | CTG | CTG | GGG | GTT | 3611 |
| Gly | Asp | Arg | Lys | Asp | Glu | Cys | Phe | Met | Tyr | Met | Ser | Leu | Leu | Gly | Val |
|     |     | 45  |     |     |     |     | 50  |     |     |     |     | 55  |     |     |     |

| GTT | GAG | GAC | AGC | GAT | CCC | CTA | GGG | CCT | CCA | ATC | GGG | CGA | GCA | TTT | GGG | 3659 |
| Val | Glu | Asp | Ser | Asp | Pro | Leu | Gly | Pro | Pro | Ile | Gly | Arg | Ala | Phe | Gly |
|     | 60  |     |     |     |     | 65  |     |     |     |     | 70  |     |     |     |     |

| TCC | CTG | CCC | TTA | GGT | GTT | GGC | AGA | TCC | ACA | GCA | AAG | CCC | GAA | AAA | CTC | 3707 |
| Ser | Leu | Pro | Leu | Gly | Val | Gly | Arg | Ser | Thr | Ala | Lys | Pro | Glu | Lys | Leu |
| 75  |     |     |     |     | 80  |     |     |     |     | 85  |     |     |     |     | 90  |

| CTC | AAA | GAG | GCC | ACT | GAG | CTT | GAC | ATA | GTT | GTT | AGA | CGT | ACA | GCA | GGG | 3755 |
| Leu | Lys | Glu | Ala | Thr | Glu | Leu | Asp | Ile | Val | Val | Arg | Arg | Thr | Ala | Gly |
|     |     |     |     | 95  |     |     |     |     | 100 |     |     |     |     | 105 |     |

| CTC | AAT | GAA | AAA | CTG | GTG | TTC | TAC | AAC | AAC | ACC | CCA | CTA | ACT | CTC | CTC | 3803 |
| Leu | Asn | Glu | Lys | Leu | Val | Phe | Tyr | Asn | Asn | Thr | Pro | Leu | Thr | Leu | Leu |
|     |     |     | 110 |     |     |     |     | 115 |     |     |     |     | 120 |     |     |

| ACA | CCT | TGG | AGA | AAG | GTC | CTA | ACA | ACA | GGG | AGT | GTC | TTC | AAC | GCA | AAC | 3851 |
| Thr | Pro | Trp | Arg | Lys | Val | Leu | Thr | Thr | Gly | Ser | Val | Phe | Asn | Ala | Asn |
|     |     | 125 |     |     |     |     | 130 |     |     |     |     | 135 |     |     |     |

| CAA | GTG | TGC | AAT | GCG | GTT | AAT | CTG | ATA | CCG | CTC | GAT | ACC | CCG | CAG | AGG | 3899 |
| Gln | Val | Cys | Asn | Ala | Val | Asn | Leu | Ile | Pro | Leu | Asp | Thr | Pro | Gln | Arg |
| 140 |     |     |     |     | 145 |     |     |     |     | 150 |     |     |     |     |     |

| TTC | CGT | GTT | GTT | TAT | ATG | AGC | ATC | ACC | CGT | CTT | TCG | GAT | AAC | GGG | TAT | 3947 |
| Phe | Arg | Val | Val | Tyr | Met | Ser | Ile | Thr | Arg | Leu | Ser | Asp | Asn | Gly | Tyr |
| 155 |     |     |     |     | 160 |     |     |     |     | 165 |     |     |     |     | 170 |

| TAC | ACC | GTT | CCT | AGA | AGA | ATG | CTG | GAA | TTC | AGA | TCG | GTC | AAT | GCA | GTG | 3995 |
| Tyr | Thr | Val | Pro | Arg | Arg | Met | Leu | Glu | Phe | Arg | Ser | Val | Asn | Ala | Val |
|     |     |     |     | 175 |     |     |     |     | 180 |     |     |     |     | 185 |     |

| GCC | TTC | AAC | CTG | CTG | GTG | ACC | CTT | AGG | ATT | GAC | AAG | GCG | ATA | GGC | CCT | 4043 |
| Ala | Phe | Asn | Leu | Leu | Val | Thr | Leu | Arg | Ile | Asp | Lys | Ala | Ile | Gly | Pro |
|     |     |     | 190 |     |     |     |     | 195 |     |     |     |     | 200 |     |     |

| GGG | AAG | ATC | ATC | GAC | AAT | ACA | GAG | CAA | CTT | CCT | GAG | GCA | ACA | TTT | ATG | 4091 |
| Gly | Lys | Ile | Ile | Asp | Asn | Thr | Glu | Gln | Leu | Pro | Glu | Ala | Thr | Phe | Met |
|     |     | 205 |     |     |     |     | 210 |     |     |     |     | 215 |     |     |     |

| GTC | CAC | ATC | GGG | AAC | TTC | AGG | AGA | AAG | AAG | AGT | GAA | GTC | TAC | TCT | GCC | 4139 |
| Val | His | Ile | Gly | Asn | Phe | Arg | Arg | Lys | Lys | Ser | Glu | Val | Tyr | Ser | Ala |
|     | 220 |     |     |     |     | 225 |     |     |     |     | 230 |     |     |     |     |

| GAT | TAT | TGC | AAA | ATG | AAA | ATC | GAA | AAG | ATG | GGC | CTG | GTT | TTT | GCA | CTT | 4187 |
| Asp | Tyr | Cys | Lys | Met | Lys | Ile | Glu | Lys | Met | Gly | Leu | Val | Phe | Ala | Leu |
| 235 |     |     |     |     | 240 |     |     |     |     | 245 |     |     |     |     | 250 |

-continued

```
GGT GGG ATA GGG GGC ACC AGT CTT CAC ATT AGA AGC ACA GGC AAA ATG      4235
Gly Gly Ile Gly Gly Thr Ser Leu His Ile Arg Ser Thr Gly Lys Met
            255                 260                 265

AGC AAG ACT CTC CAT GCA CAA CTC GGG TTC AAG AAG ACC TTA TGT TAC      4283
Ser Lys Thr Leu His Ala Gln Leu Gly Phe Lys Lys Thr Leu Cys Tyr
        270                 275                 280

CCG CTG ATG GAT ATC AAT GAA GAC CTT AAT CGA TTA CTC TGG AGG AGC      4331
Pro Leu Met Asp Ile Asn Glu Asp Leu Asn Arg Leu Leu Trp Arg Ser
        285                 290                 295

AGA TGC AAG ATA GTA AGA ATC CAG GCA GTT TTG CAG CCA TCA GTT CCT      4379
Arg Cys Lys Ile Val Arg Ile Gln Ala Val Leu Gln Pro Ser Val Pro
    300                 305                 310

CAA GAA TTC CGC ATT TAC GAC GAC GTG ATC ATA AAT GAT GAC CAA GGA      4427
Gln Glu Phe Arg Ile Tyr Asp Asp Val Ile Ile Asn Asp Asp Gln Gly
315                 320                 325                 330

CTA TTC AAA GTT CTG TAGACCGTAG TGCCCAGCAA TGCCCGAAAA CGACCCCCCT      4482
Leu Phe Lys Val Leu
            335

CACAATGACA GCCAGAAGGC CCGGACAAAA AAGCCCCCTC CGAAAGACTC CACTGACCAA    4542

GCGAGAGGCC AGCCAGCAGC CGACGGCAAG CACGAACACC AGGCGGCCCC AGCACAGAAC    4602

AGCCCTGATA CAAGGCCACC ACCAGCCACC CCAATCTGCA TCCTCCTCGT GGGACCCCCG    4662

AGGACCAACC CCCAAGGCTG CCCCCGATCC AAACCACCAA CCGCATCCCC ACCACCCCCG    4722

GGAAAGAAAC CCCCAGCAAT TGGAAGGCCC CTCCCCCTCT TCCTCAACAC AAGAACTCCA    4782

CAACCGAACC GCACAAGCGA CCGAGGTGAC CCAACCGCGC GGCATCCGAC TCCCTAGACA    4842

GATCCTCTCT CCCCGGCAAA CTAAACAAAA CTTAGGGCCA AGGAACATAC ACACCCAACA    4902

GAACCCAGAC CCCGGCCCAC GGCGCCGCGC CCCCAACCCC CGACAACCAG AGGGAGCCCC    4962

CAACCAATCC CGCCGGCTCC CCCGGTGCCC ACAGGCAGGG ACACCAACCC CGAACAGAC     5022

CCAGCACCCA ACCATCGACA ATCCAAGACG GGGGGCCCC CCCAAAAAAA GGCCCCCAGG     5082

GGCCGACAGC CAGCACCGCG AGGAAGCCCA CCCACCCCAC ACACGACCAC GGCAACCAAA    5142

CCAGAACCCA GACCACCCTG GCCACCAGCT CCCAGACTCG GCCATCACCC CGCAGAAAGG    5202

AAAGGCCACA ACCCGCGCAC CCCAGCCCCG ATCCGGCGGG GAGCCACCCA ACCCGAACCA    5262

GCACCCAAGA GCGATCCCCG AAGGACCCCC GAACCGCAAA GGACATCAGT ATCCCACAGC    5322

CTCTCCAAGT CCCCCGGTCT CCTCCTCTTC TCGAAGGGAC CAAAAGATCA ATCCACCACA    5382

CCCGACGACA CTCAACTCCC CACCCCTAAA GGAGACACCG GGAATCCCAG AATCAAGACT    5442

CATCCAATGT CCATC ATG GGT CTC AAG GTG AAC GTC TCT GCC ATA TTC ATG    5493
                Met Gly Leu Lys Val Asn Val Ser Ala Ile Phe Met
                 1               5                  10

GCA GTA CTG TTA ACT CTC CAA ACA CCC ACC GGT CAA ATC CAT TGG GGC      5541
Ala Val Leu Leu Thr Leu Gln Thr Pro Thr Gly Gln Ile His Trp Gly
         15                 20                  25

AAT CTC TCT AAG ATA GGG GTG GTA GGA ATA GGA AGT GCA AGC TAC AAA      5589
Asn Leu Ser Lys Ile Gly Val Val Gly Ile Gly Ser Ala Ser Tyr Lys
        30                  35                  40

GTT ATG ACT CGT TCC AGC CAT CAA TCA TTA GTC ATA AAA TTA ATG CCC      5637
Val Met Thr Arg Ser Ser His Gln Ser Leu Val Ile Lys Leu Met Pro
45                  50                  55                  60

AAT ATA ACT CTC CTC AAT AAC TGC ACG AGG GTA GAG ATT GCA GAA TAC      5685
Asn Ile Thr Leu Leu Asn Asn Cys Thr Arg Val Glu Ile Ala Glu Tyr
            65                  70                  75

AGG AGA CTA CTG AGA ACA GTT TTG GAA CCA ATT AGA GAT GCA CTT AAT      5733
Arg Arg Leu Leu Arg Thr Val Leu Glu Pro Ile Arg Asp Ala Leu Asn
            80                  85                  90
```

```
GCA ATG ACC CAG AAT ATA AGA CCG GTT CAG AGT GTA GCT TCA AGT AGG    5781
Ala Met Thr Gln Asn Ile Arg Pro Val Gln Ser Val Ala Ser Ser Arg
        95                  100                 105

AGA CAC AAG AGA TTT GCG GGA GTA GTC CTG GCA GGT GCG GCC CTA GGC    5829
Arg His Lys Arg Phe Ala Gly Val Val Leu Ala Gly Ala Ala Leu Gly
        110                 115                 120

GTT GCC ACA GCT GCT CAG ATA ACA GCC GGC ATT GCA CTT CAC CAG TCC    5877
Val Ala Thr Ala Ala Gln Ile Thr Ala Gly Ile Ala Leu His Gln Ser
125                 130                 135                 140

ATG CTG AAC TCT CAA GCC ATC GAC AAT CTG AGA GCG AGC CTG GAA ACT    5925
Met Leu Asn Ser Gln Ala Ile Asp Asn Leu Arg Ala Ser Leu Glu Thr
                145                 150                 155

ACT AAT CAG GCA ATT GAG GCA ATC AGA CAA GCA GGG CAG GAG ATG ATA    5973
Thr Asn Gln Ala Ile Glu Ala Ile Arg Gln Ala Gly Gln Glu Met Ile
        160                 165                 170

TTG GCT GTT CAG GGT GTC CAA GAC TAC ATC AAT AAT GAG CTG ATA CCG    6021
Leu Ala Val Gln Gly Val Gln Asp Tyr Ile Asn Asn Glu Leu Ile Pro
        175                 180                 185

TCT ATG AAC CAA CTA TCT TGT GAT TTA ATC GGC CAG AAG CTC GGG CTC    6069
Ser Met Asn Gln Leu Ser Cys Asp Leu Ile Gly Gln Lys Leu Gly Leu
        190                 195                 200

AAA TTG CTC AGA TAC TAT ACA GAA ATC CTG TCA TTA TTT GGC CCC AGC    6117
Lys Leu Leu Arg Tyr Tyr Thr Glu Ile Leu Ser Leu Phe Gly Pro Ser
205                 210                 215                 220

TTA CGG GAC CCC ATA TCT GCG GAG ATA TCT ATC CAG GCT TTG AGC TAT    6165
Leu Arg Asp Pro Ile Ser Ala Glu Ile Ser Ile Gln Ala Leu Ser Tyr
                225                 230                 235

GCG CTT GGA GGA GAC ATC AAT AAG GTG TTA GAA AAG CTC GGA TAC AGT    6213
Ala Leu Gly Gly Asp Ile Asn Lys Val Leu Glu Lys Leu Gly Tyr Ser
        240                 245                 250

GGA GGT GAT TTA CTG GGC ATC TTA GAG AGC AGA GGA ATA AAG GCC CGG    6261
Gly Gly Asp Leu Leu Gly Ile Leu Glu Ser Arg Gly Ile Lys Ala Arg
        255                 260                 265

ATA ACT CAC GTC GAC ACA GAG TCC TAC TTA ATT GTC CTC AGT ATA GCC    6309
Ile Thr His Val Asp Thr Glu Ser Tyr Leu Ile Val Leu Ser Ile Ala
        270                 275                 280

TAT CCG ACG CTG TCC GAG ATT AAG GGG GTG ATT GTC CAC CGG CTA GAG    6357
Tyr Pro Thr Leu Ser Glu Ile Lys Gly Val Ile Val His Arg Leu Glu
285                 290                 295                 300

GGG GTC TCG TAC AAC ATA GGC TCT CAA GAG TGG TAT ACC ACT GTG CCC    6405
Gly Val Ser Tyr Asn Ile Gly Ser Gln Glu Trp Tyr Thr Thr Val Pro
                305                 310                 315

AAG TAT GTT GCA ACC CAA GGG TAC CTT ATC TCG AAT TTT GAT GAG TCA    6453
Lys Tyr Val Ala Thr Gln Gly Tyr Leu Ile Ser Asn Phe Asp Glu Ser
        320                 325                 330

TCG TGT ACT TTC ATG CCA GAG GGG ACT GTG TGC AGC CAA AAT GCC TTG    6501
Ser Cys Thr Phe Met Pro Glu Gly Thr Val Cys Ser Gln Asn Ala Leu
        335                 340                 345

TAC CCG ATG AGT CCT CTG CTC CAA GAA TGC CTC CGG GGG TCC ACC AAG    6549
Tyr Pro Met Ser Pro Leu Leu Gln Glu Cys Leu Arg Gly Ser Thr Lys
350                 355                 360

TCC TGT GCT CGT ACA CTC GTA TCC GGG TCT TTT GGG AAC CGG TTC ATT    6597
Ser Cys Ala Arg Thr Leu Val Ser Gly Ser Phe Gly Asn Arg Phe Ile
365                 370                 375                 380

TTA TCA CAA GGG AAC CTA ATA GCC AAT TGT GCA TCA ATC CTT TGC AAG    6645
Leu Ser Gln Gly Asn Leu Ile Ala Asn Cys Ala Ser Ile Leu Cys Lys
                385                 390                 395

TGT TAC ACA ACA GGA ACG ATC ATT AAT CAA GAC CCT GAC AAG ATC CTA    6693
Cys Tyr Thr Thr Gly Thr Ile Ile Asn Gln Asp Pro Asp Lys Ile Leu
        400                 405                 410
```

```
ACA TAC ATT GCT GCC GAT CAC TGC CCG GTA GTC GAG GTG AAC GGC GTG       6741
Thr Tyr Ile Ala Ala Asp His Cys Pro Val Val Glu Val Asn Gly Val
        415             420                 425

ACC ATC CAA GTC GGG AGC AGG AGG TAT CCA GAC GCT GTG TAC TTG CAC       6789
Thr Ile Gln Val Gly Ser Arg Arg Tyr Pro Asp Ala Val Tyr Leu His
        430             435                 440

AGA ATT GAC CTC GGT CCT CCC ATA TTA TTG GAG AGG TTG GAC GTA GGG       6837
Arg Ile Asp Leu Gly Pro Pro Ile Leu Leu Glu Arg Leu Asp Val Gly
445             450                 455                         460

ACA AAT CTG GGG AAT GCA ATT GCT AAG TTG GAG GAT GCC AAG GAA TTG       6885
Thr Asn Leu Gly Asn Ala Ile Ala Lys Leu Glu Asp Ala Lys Glu Leu
                    465                 470                 475

TTG GAG TCA TCG GAC CAG ATA TTG AGG AGT ATG AAA GGT TTA TCG AGC       6933
Leu Glu Ser Ser Asp Gln Ile Leu Arg Ser Met Lys Gly Leu Ser Ser
                480                 485                 490

ACT TGC ATA GTC TAC ATC CTG ATT GCA GTG TGT CTT GGA GGG TTG ATA       6981
Thr Cys Ile Val Tyr Ile Leu Ile Ala Val Cys Leu Gly Gly Leu Ile
            495                 500                 505

GGG ATC CCC GCT TTA ATA TGT TGC TGC AGG GGG CGT TGT AAC AAA AAG       7029
Gly Ile Pro Ala Leu Ile Cys Cys Cys Arg Gly Arg Cys Asn Lys Lys
        510                 515                 520

GGA GAA CAA GTT GGT ATG TCA AGA CCA GGC CTA AAG CCT GAT CTT ACG       7077
Gly Glu Gln Val Gly Met Ser Arg Pro Gly Leu Lys Pro Asp Leu Thr
525             530                 535                         540

GGA ACA TCA AAA TCC TAT GTA AGG TCG CTC TGATCCTCTA CAACTCTTGA         7127
Gly Thr Ser Lys Ser Tyr Val Arg Ser Leu
                    545             550

AACACAAATG TCCCACAAGT CTCCTCTTCG TCATCAAGCA ACCACCGCAC CCAGCATCAA     7187

GCCCACCTGA AATTATCTCC GGCTTCCCTC TGGCCGAACA ATATCGGTAG TTAATTAAAA     7247

CTTAGGGTGC AAGATCATCC ACA ATG TCA CCA CAA CGA GAC CGG ATA AAT        7297
                          Met Ser Pro Gln Arg Asp Arg Ile Asn
                          1                   5

GCC TTC TAC AAA GAT AAC CCC CAT CCC AAG GGA AGT AGG ATA GTC ATT       7345
Ala Phe Tyr Lys Asp Asn Pro His Pro Lys Gly Ser Arg Ile Val Ile
10              15                  20                          25

AAC AGA GAA CAT CTT ATG ATT GAT AGA CCT TAT GTT TTG CTG GCT GTT       7393
Asn Arg Glu His Leu Met Ile Asp Arg Pro Tyr Val Leu Leu Ala Val
            30                  35                  40

CTG TTT GTC ATG TTT CTG AGC TTG ATC GGG TTG CTA GCC ATT GCA GGC       7441
Leu Phe Val Met Phe Leu Ser Leu Ile Gly Leu Leu Ala Ile Ala Gly
                45                  50                  55

ATT AGA CTT CAT CGG GCA GCC ATC TAC ACC GCA GAG ATC CAT AAA AGC       7489
Ile Arg Leu His Arg Ala Ala Ile Tyr Thr Ala Glu Ile His Lys Ser
            60                  65                  70

CTC AGC ACC AAT CTA GAT GTA ACT AAC TCA ATC GAG CAT CAG GTC AAG       7537
Leu Ser Thr Asn Leu Asp Val Thr Asn Ser Ile Glu His Gln Val Lys
75              80                  85

GAC GTG CTG ACA CCA CTC TTC AAA ATC ATC GGT GAT GAA GTG GGC CTG       7585
Asp Val Leu Thr Pro Leu Phe Lys Ile Ile Gly Asp Glu Val Gly Leu
        90                  95                  100             105

AGG ACA CCT CAG AGA TTC ACT GAC CTA GTG AAA TTC ATC TCT GAC AAG       7633
Arg Thr Pro Gln Arg Phe Thr Asp Leu Val Lys Phe Ile Ser Asp Lys
                    110                 115                 120

ATT AAA TTC CTT AAT CCG GAT AGG GAG TAC GAC TTC AGA GAT CTC ACT       7681
Ile Lys Phe Leu Asn Pro Asp Arg Glu Tyr Asp Phe Arg Asp Leu Thr
                125                 130                 135

TGG TGT ATG AAC CCG CCA GAG AGA ATC AAA TTG GAT TAT GAT CAA TAC       7729
Trp Cys Met Asn Pro Pro Glu Arg Ile Lys Leu Asp Tyr Asp Gln Tyr
            140                 145                 150
```

| | | | | | | | | | | | | | | | | |
|---|---|---|---|---|---|---|---|---|---|---|---|---|---|---|---|---|
| TGT | GCA | GAT | GTG | GCT | GCT | GAA | GAG | CTC | ATG | AAT | GCA | TTG | GTG | AAC | TCA | 7777 |
| Cys | Ala | Asp | Val | Ala | Ala | Glu | Glu | Leu | Met | Asn | Ala | Leu | Val | Asn | Ser | |
| 155 | | | | | 160 | | | | | 165 | | | | | | |
| ACT | CTA | CTG | GAG | ACC | AGA | ACA | ACC | AAT | CAG | TTC | CTA | GCT | GTC | TCA | AAG | 7825 |
| Thr | Leu | Leu | Glu | Thr | Arg | Thr | Thr | Asn | Gln | Phe | Leu | Ala | Val | Ser | Lys | |
| 170 | | | | | 175 | | | | | 180 | | | | | 185 | |
| GGA | AAC | TGC | TCA | GGG | CCC | ACT | ACA | ATC | AGA | GGT | CAA | TTC | TCA | AAC | ATG | 7873 |
| Gly | Asn | Cys | Ser | Gly | Pro | Thr | Thr | Ile | Arg | Gly | Gln | Phe | Ser | Asn | Met | |
| | | | | 190 | | | | | 195 | | | | | | 200 | |
| TCG | CTG | TCC | CTG | TTA | GAC | TTG | TAT | TTA | GGT | CGA | GGT | TAC | AAT | GTG | TCA | 7921 |
| Ser | Leu | Ser | Leu | Leu | Asp | Leu | Tyr | Leu | Gly | Arg | Gly | Tyr | Asn | Val | Ser | |
| | | | | 205 | | | | | 210 | | | | | 215 | | |
| TCT | ATA | GTC | ACT | ATG | ACA | TCC | CAG | GGA | ATG | TAT | GGG | GGA | ACT | TAC | CTA | 7969 |
| Ser | Ile | Val | Thr | Met | Thr | Ser | Gln | Gly | Met | Tyr | Gly | Gly | Thr | Tyr | Leu | |
| | | 220 | | | | | 225 | | | | | 230 | | | | |
| GTG | GAA | AAG | CCT | AAT | CTG | AGC | AGC | AAA | AGG | TCA | GAG | TTG | TCA | CAA | CTG | 8017 |
| Val | Glu | Lys | Pro | Asn | Leu | Ser | Ser | Lys | Arg | Ser | Glu | Leu | Ser | Gln | Leu | |
| | 235 | | | | | 240 | | | | | 245 | | | | | |
| AGC | ATG | TAC | CGA | GTG | TTT | GAA | GTA | GGT | GTT | ATC | AGA | AAT | CCG | GGT | TTG | 8065 |
| Ser | Met | Tyr | Arg | Val | Phe | Glu | Val | Gly | Val | Ile | Arg | Asn | Pro | Gly | Leu | |
| 250 | | | | | 255 | | | | | 260 | | | | | 265 | |
| GGG | GCT | CCG | GTG | TTC | CAT | ATG | ACA | AAC | TAT | CTT | GAG | CAA | CCA | GTC | AGT | 8113 |
| Gly | Ala | Pro | Val | Phe | His | Met | Thr | Asn | Tyr | Leu | Glu | Gln | Pro | Val | Ser | |
| | | | | 270 | | | | | 275 | | | | | 280 | | |
| AAT | GAT | CTC | AGC | AAC | TGT | ATG | GTG | GCT | TTG | GGG | GAG | CTC | AAA | CTC | GCA | 8161 |
| Asn | Asp | Leu | Ser | Asn | Cys | Met | Val | Ala | Leu | Gly | Glu | Leu | Lys | Leu | Ala | |
| | | | 285 | | | | | 290 | | | | | 295 | | | |
| GCC | CTT | TGT | CAC | CGG | GAA | GAT | TCT | ATC | ACA | ATT | CCC | TAT | CAG | GGA | TCA | 8209 |
| Ala | Leu | Cys | His | Arg | Glu | Asp | Ser | Ile | Thr | Ile | Pro | Tyr | Gln | Gly | Ser | |
| | | 300 | | | | | 305 | | | | | 310 | | | | |
| GGG | AAA | GGT | GTC | AGC | TTC | CAG | CTC | GTC | AAG | CTA | GGT | GTC | TGG | AAA | TCC | 8257 |
| Gly | Lys | Gly | Val | Ser | Phe | Gln | Leu | Val | Lys | Leu | Gly | Val | Trp | Lys | Ser | |
| | 315 | | | | | 320 | | | | | 325 | | | | | |
| CCA | ACC | GAC | ATG | CAA | TCC | TGG | GTC | ACC | TTA | TCA | ACG | GAT | GAT | CCA | GTG | 8305 |
| Pro | Thr | Asp | Met | Gln | Ser | Trp | Val | Thr | Leu | Ser | Thr | Asp | Asp | Pro | Val | |
| 330 | | | | | 335 | | | | | 340 | | | | | 345 | |
| ATA | GAC | AGG | CTT | TAC | CTC | TCA | TCT | CAC | AGA | GGT | GTT | ATC | GCT | GAC | AAT | 8353 |
| Ile | Asp | Arg | Leu | Tyr | Leu | Ser | Ser | His | Arg | Gly | Val | Ile | Ala | Asp | Asn | |
| | | | | 350 | | | | | 355 | | | | | | 360 | |
| CAA | GCA | AAA | TGG | GCT | GTC | CCG | ACA | ACA | CGA | ACA | GAT | GAC | AAG | TTG | CGA | 8401 |
| Gln | Ala | Lys | Trp | Ala | Val | Pro | Thr | Thr | Arg | Thr | Asp | Asp | Lys | Leu | Arg | |
| | | | 365 | | | | | 370 | | | | | 375 | | | |
| ATG | GAG | ACA | TGC | TTC | CAA | CAG | GCG | TGT | AAG | GGT | AAA | ATC | CAA | GCA | CTC | 8449 |
| Met | Glu | Thr | Cys | Phe | Gln | Gln | Ala | Cys | Lys | Gly | Lys | Ile | Gln | Ala | Leu | |
| | | 380 | | | | | 385 | | | | | 390 | | | | |
| TGC | GAG | AAT | CCC | GAG | TGG | GCA | CCA | TTG | AAG | GAT | AAC | AGG | ATT | CCT | TCA | 8497 |
| Cys | Glu | Asn | Pro | Glu | Trp | Ala | Pro | Leu | Lys | Asp | Asn | Arg | Ile | Pro | Ser | |
| | 395 | | | | | 400 | | | | | 405 | | | | | |
| TAC | GGG | GTC | TTG | TCT | GTT | GAT | CTG | AGT | CTG | ACA | GTT | GAG | CTT | AAA | ATC | 8545 |
| Tyr | Gly | Val | Leu | Ser | Val | Asp | Leu | Ser | Leu | Thr | Val | Glu | Leu | Lys | Ile | |
| 410 | | | | | 415 | | | | | 420 | | | | | 425 | |
| AAA | ATT | GCT | TCG | GGA | TTC | GGG | CCA | TTG | ATC | ACA | CAC | GGT | TCA | GGG | ATG | 8593 |
| Lys | Ile | Ala | Ser | Gly | Phe | Gly | Pro | Leu | Ile | Thr | His | Gly | Ser | Gly | Met | |
| | | | | 430 | | | | | 435 | | | | | | 440 | |
| GAC | CTA | TAC | AAA | TCC | AAC | CAC | AAC | AAT | GTG | TAT | TGG | CTG | ACT | ATC | CCA | 8641 |
| Asp | Leu | Tyr | Lys | Ser | Asn | His | Asn | Asn | Val | Tyr | Trp | Leu | Thr | Ile | Pro | |
| | | | 445 | | | | | 450 | | | | | 455 | | | |
| CCA | ATG | AAG | AAC | CTA | GCC | TTA | GGT | GTA | ATC | AAC | ACA | TTG | GAG | TGG | ATA | 8689 |
| Pro | Met | Lys | Asn | Leu | Ala | Leu | Gly | Val | Ile | Asn | Thr | Leu | Glu | Trp | Ile | |
| | | 460 | | | | | 465 | | | | | 470 | | | | |

| | | | | | | | | | | | | | | | | |
|---|---|---|---|---|---|---|---|---|---|---|---|---|---|---|---|---|
| CCG | AGA | TTC | AAG | GTT | AGT | CCC | TAC | CTC | TTC | AAT | GTC | CCA | ATT | AAG | GAA | 8737 |
| Pro | Arg | Phe | Lys | Val | Ser | Pro | Tyr | Leu | Phe | Asn | Val | Pro | Ile | Lys | Glu | |
| 475 | | | | | 480 | | | | | 485 | | | | | | |
| GCA | GGC | GAA | GAC | TGC | CAT | GCC | CCA | ACA | TAC | CTA | CCT | GCG | GAG | GTG | GAT | 8785 |
| Ala | Gly | Glu | Asp | Cys | His | Ala | Pro | Thr | Tyr | Leu | Pro | Ala | Glu | Val | Asp | |
| 490 | | | | 495 | | | | | 500 | | | | | | 505 | |
| GGT | GAT | GTC | AAA | CTC | AGT | TCC | AAT | CTG | GTG | ATT | CTA | CCT | GGT | CAA | GAT | 8833 |
| Gly | Asp | Val | Lys | Leu | Ser | Ser | Asn | Leu | Val | Ile | Leu | Pro | Gly | Gln | Asp | |
| | | | | 510 | | | | | 515 | | | | | 520 | | |
| CTC | CAA | TAT | GTT | TTG | GCA | ACC | TAC | GAT | ACT | TCC | AGG | GTT | GAA | CAT | GCT | 8881 |
| Leu | Gln | Tyr | Val | Leu | Ala | Thr | Tyr | Asp | Thr | Ser | Arg | Val | Glu | His | Ala | |
| | | | 525 | | | | 530 | | | | | 535 | | | | |
| GTG | GTT | TAT | TAC | GTT | TAC | AGC | CCA | AGC | CGC | TCA | TTT | TCT | TAC | TTT | TAT | 8929 |
| Val | Val | Tyr | Tyr | Val | Tyr | Ser | Pro | Ser | Arg | Ser | Phe | Ser | Tyr | Phe | Tyr | |
| | | 540 | | | | | 545 | | | | | 550 | | | | |
| CCT | TTT | AGG | TTG | CCT | ATA | AAG | GGG | GTC | CCC | ATC | GAA | TTA | CAA | GTG | GAA | 8977 |
| Pro | Phe | Arg | Leu | Pro | Ile | Lys | Gly | Val | Pro | Ile | Glu | Leu | Gln | Val | Glu | |
| | 555 | | | | | 560 | | | | | 565 | | | | | |
| TGC | TTC | ACA | TGG | GAC | CAA | AAA | CTC | TGG | TGC | CGT | CAC | TTC | TGT | GTG | CTT | 9025 |
| Cys | Phe | Thr | Trp | Asp | Gln | Lys | Leu | Trp | Cys | Arg | His | Phe | Cys | Val | Leu | |
| 570 | | | | | 575 | | | | | 580 | | | | | 585 | |
| GCG | GAC | TCA | GAA | TCT | GGT | GGA | CAT | ATC | ACT | CAC | TCT | GGG | ATG | GTG | GGC | 9073 |
| Ala | Asp | Ser | Glu | Ser | Gly | Gly | His | Ile | Thr | His | Ser | Gly | Met | Val | Gly | |
| | | | | 590 | | | | | 595 | | | | | 600 | | |
| ATG | GGA | GTC | AGC | TGC | ACA | GTC | ACC | CGG | GAA | GAT | GGA | ACC | AAT | CGC | AGA | 9121 |
| Met | Gly | Val | Ser | Cys | Thr | Val | Thr | Arg | Glu | Asp | Gly | Thr | Asn | Arg | Arg | |
| | | | 605 | | | | | 610 | | | | | 615 | | | |

TAGGGCTGCT AGTGAACTAA TCTCATGATG TCACCCAGAC ATCAGGCATA CCCACTAGTG   9181

TGAAATAGAC ATCAGAATTA AGAAAAACGT AGGGTCCAAG TGGTTCCCCG TT ATG   9236
                                                            Met
                                                             1

| | | | | | | | | | | | | | | | | |
|---|---|---|---|---|---|---|---|---|---|---|---|---|---|---|---|---|
| GAC | TCG | CTA | TCT | GTC | AAC | CAG | ATC | TTA | TAC | CCT | GAA | GTT | CAC | CTA | GAT | 9284 |
| Asp | Ser | Leu | Ser | Val | Asn | Gln | Ile | Leu | Tyr | Pro | Glu | Val | His | Leu | Asp | |
| | | | 5 | | | | | 10 | | | | | 15 | | | |
| AGC | CCG | ATA | GTT | ACC | AAT | AAG | ATA | GTA | GCC | ATC | CTG | GAG | TAT | GCT | CGA | 9332 |
| Ser | Pro | Ile | Val | Thr | Asn | Lys | Ile | Val | Ala | Ile | Leu | Glu | Tyr | Ala | Arg | |
| | | 20 | | | | | 25 | | | | | 30 | | | | |
| GTT | CCT | CAC | GCT | TAC | AGC | CTG | GAG | GAC | CCT | ACA | CTG | TGT | CAG | AAC | ATC | 9380 |
| Val | Pro | His | Ala | Tyr | Ser | Leu | Glu | Asp | Pro | Thr | Leu | Cys | Gln | Asn | Ile | |
| 35 | | | | | 40 | | | | | 45 | | | | | | |
| AAG | CAC | CGC | CTA | AAA | AAC | GGA | TTT | TCC | AAC | CAA | ATG | ATT | ATA | AAC | AAT | 9428 |
| Lys | His | Arg | Leu | Lys | Asn | Gly | Phe | Ser | Asn | Gln | Met | Ile | Ile | Asn | Asn | |
| 50 | | | | | 55 | | | | | 60 | | | | | 65 | |
| GTG | GAA | GTT | GGG | AAT | GTC | ATC | AAG | TCC | AAG | CTT | AGG | AGT | TAT | CCG | GCC | 9476 |
| Val | Glu | Val | Gly | Asn | Val | Ile | Lys | Ser | Lys | Leu | Arg | Ser | Tyr | Pro | Ala | |
| | | | | 70 | | | | | 75 | | | | | 80 | | |
| CAC | TCT | CAT | ATT | CCA | TAT | CCA | AAT | TGT | AAT | CAG | GAT | TTA | TTT | AAC | ATA | 9524 |
| His | Ser | His | Ile | Pro | Tyr | Pro | Asn | Cys | Asn | Gln | Asp | Leu | Phe | Asn | Ile | |
| | | | 85 | | | | | 90 | | | | | 95 | | | |
| GAA | GAC | AAA | GAG | TCA | ACG | AGG | AAG | ATC | CGT | GAA | CTC | CTC | AAA | AAG | GGG | 9572 |
| Glu | Asp | Lys | Glu | Ser | Thr | Arg | Lys | Ile | Arg | Glu | Leu | Leu | Lys | Lys | Gly | |
| | | 100 | | | | | 105 | | | | | 110 | | | | |
| AAT | TCG | CTG | TAC | TCC | AAA | GTC | AGT | GAT | AAG | GTT | TTC | CAA | TGC | TTA | AGG | 9620 |
| Asn | Ser | Leu | Tyr | Ser | Lys | Val | Ser | Asp | Lys | Val | Phe | Gln | Cys | Leu | Arg | |
| | 115 | | | | | 120 | | | | | 125 | | | | | |
| GAC | ACT | AAC | TCA | CGG | CTT | GGC | CTA | GGC | TCC | GAA | TTG | AGG | GAG | GAC | ATC | 9668 |
| Asp | Thr | Asn | Ser | Arg | Leu | Gly | Leu | Gly | Ser | Glu | Leu | Arg | Glu | Asp | Ile | |
| 130 | | | | | 135 | | | | | 140 | | | | | 145 | |
| AAG | GAG | AAA | GTT | ATT | AAC | TTG | GGA | GTT | TAC | ATG | CAC | AGC | TCC | CAG | TGG | 9716 |
| Lys | Glu | Lys | Val | Ile | Asn | Leu | Gly | Val | Tyr | Met | His | Ser | Ser | Gln | Trp | |

|     |     |     |     |     |     |     |     |     |     |     |     |     |     |     |     |       |
|-----|-----|-----|-----|-----|-----|-----|-----|-----|-----|-----|-----|-----|-----|-----|-----|-------|
|     |     |     |     | 150 |     |     |     | 155 |     |     |     | 160 |     |     |     |       |
| TTT | GAG | CCA | TTT | CTG | TTT | TGG | TTT | ACA | GTC | AAG | ACT | GAG | ATG | AGG | TCA | 9764  |
| Phe | Glu | Pro | Phe | Leu | Phe | Trp | Phe | Thr | Val | Lys | Thr | Glu | Met | Arg | Ser |       |
|     |     |     | 165 |     |     |     | 170 |     |     |     |     | 175 |     |     |     |       |
| GTG | ATT | AAA | TCA | CAA | ACC | CAT | ACT | TGC | CAT | AGG | AGG | AGA | CAC | ACA | CCT | 9812  |
| Val | Ile | Lys | Ser | Gln | Thr | His | Thr | Cys | His | Arg | Arg | Arg | His | Thr | Pro |       |
|     |     | 180 |     |     |     |     | 185 |     |     |     |     | 190 |     |     |     |       |
| GTA | TTC | TTC | ACT | GGT | AGT | TCA | GTT | GAG | TTG | CTA | ATC | TCT | CGT | GAC | CTT | 9860  |
| Val | Phe | Phe | Thr | Gly | Ser | Ser | Val | Glu | Leu | Leu | Ile | Ser | Arg | Asp | Leu |       |
|     |     | 195 |     |     |     | 200 |     |     |     |     | 205 |     |     |     |     |       |
| GTT | GCT | ATA | ATC | AGT | AAA | GAG | TCT | CAA | CAT | GTA | TAT | TAC | CTG | ACA | TTT | 9908  |
| Val | Ala | Ile | Ile | Ser | Lys | Glu | Ser | Gln | His | Val | Tyr | Tyr | Leu | Thr | Phe |       |
| 210 |     |     |     |     | 215 |     |     |     |     | 220 |     |     |     |     | 225 |       |
| GAA | CTG | GTT | TTG | ATG | TAT | TGT | GAT | GTC | ATA | GAG | GGG | AGG | TTA | ATG | ACA | 9956  |
| Glu | Leu | Val | Leu | Met | Tyr | Cys | Asp | Val | Ile | Glu | Gly | Arg | Leu | Met | Thr |       |
|     |     |     |     | 230 |     |     |     |     | 235 |     |     |     |     | 240 |     |       |
| GAG | ACC | GCT | ATG | ACT | ATT | GAT | GCT | AGG | TAT | ACA | GAG | CTT | CTA | GGA | AGA | 10004 |
| Glu | Thr | Ala | Met | Thr | Ile | Asp | Ala | Arg | Tyr | Thr | Glu | Leu | Leu | Gly | Arg |       |
|     |     |     |     | 245 |     |     |     |     | 250 |     |     |     |     | 255 |     |       |
| GTC | AGA | TAC | ATG | TGG | AAA | CTG | ATA | GAT | GGT | TTC | TTC | CCT | GCA | CTC | GGG | 10052 |
| Val | Arg | Tyr | Met | Trp | Lys | Leu | Ile | Asp | Gly | Phe | Phe | Pro | Ala | Leu | Gly |       |
|     |     | 260 |     |     |     |     | 265 |     |     |     |     | 270 |     |     |     |       |
| AAT | CCA | ACT | TAT | CAA | ATT | GTA | GCC | ATG | CTG | GAG | CCT | CTT | TCA | CTT | GCT | 10100 |
| Asn | Pro | Thr | Tyr | Gln | Ile | Val | Ala | Met | Leu | Glu | Pro | Leu | Ser | Leu | Ala |       |
| 275 |     |     |     |     | 280 |     |     |     |     | 285 |     |     |     |     |     |       |
| TAC | CTG | CAG | CTG | AGG | GAT | ATA | ACA | GTA | GAA | CTC | AGA | GGT | GCT | TTC | CTT | 10148 |
| Tyr | Leu | Gln | Leu | Arg | Asp | Ile | Thr | Val | Glu | Leu | Arg | Gly | Ala | Phe | Leu |       |
| 290 |     |     |     |     | 295 |     |     |     |     | 300 |     |     |     |     | 305 |       |
| AAC | CAC | TGC | TTT | ACT | GAA | ATA | CAT | GAT | GTT | CTT | GAC | CAA | AAC | GGG | TTT | 10196 |
| Asn | His | Cys | Phe | Thr | Glu | Ile | His | Asp | Val | Leu | Asp | Gln | Asn | Gly | Phe |       |
|     |     |     |     | 310 |     |     |     |     | 315 |     |     |     |     | 320 |     |       |
| TCT | GAT | GAA | GGT | ACT | TAT | CAT | GAG | TTA | ATT | GAA | GCT | CTA | GAT | TAC | ATT | 10244 |
| Ser | Asp | Glu | Gly | Thr | Tyr | His | Glu | Leu | Ile | Glu | Ala | Leu | Asp | Tyr | Ile |       |
|     |     |     | 325 |     |     |     |     | 330 |     |     |     |     | 335 |     |     |       |
| TTC | ATA | ACT | GAT | GAC | ATA | CAT | CTG | ACA | GGG | GAG | ATT | TTC | TCA | TTT | TTC | 10292 |
| Phe | Ile | Thr | Asp | Asp | Ile | His | Leu | Thr | Gly | Glu | Ile | Phe | Ser | Phe | Phe |       |
|     |     | 340 |     |     |     |     | 345 |     |     |     |     | 350 |     |     |     |       |
| AGA | AGT | TTC | GGC | CAC | CCC | AGA | CTT | GAA | GCA | GTA | ACG | GCT | GCT | GAA | AAT | 10340 |
| Arg | Ser | Phe | Gly | His | Pro | Arg | Leu | Glu | Ala | Val | Thr | Ala | Ala | Glu | Asn |       |
| 355 |     |     |     |     | 360 |     |     |     |     | 365 |     |     |     |     |     |       |
| GTT | AGG | AAA | TAC | ATG | AAT | CAG | CCT | AAA | GTC | ATT | GTG | TAT | GAG | ACT | CTG | 10388 |
| Val | Arg | Lys | Tyr | Met | Asn | Gln | Pro | Lys | Val | Ile | Val | Tyr | Glu | Thr | Leu |       |
| 370 |     |     |     |     | 375 |     |     |     |     | 380 |     |     |     |     | 385 |       |
| ATG | AAA | GGT | CAT | GCC | ATA | TTT | TGT | GGA | ATC | ATA | ATC | AAC | GGC | TAT | CGT | 10436 |
| Met | Lys | Gly | His | Ala | Ile | Phe | Cys | Gly | Ile | Ile | Ile | Asn | Gly | Tyr | Arg |       |
|     |     |     |     | 390 |     |     |     |     | 395 |     |     |     |     | 400 |     |       |
| GAC | AGG | CAC | GGA | GGC | AGT | TGG | CCA | CCG | CTG | ACC | CTC | CCC | CTG | CAT | GCT | 10484 |
| Asp | Arg | His | Gly | Gly | Ser | Trp | Pro | Pro | Leu | Thr | Leu | Pro | Leu | His | Ala |       |
|     |     |     |     | 405 |     |     |     |     | 410 |     |     |     |     | 415 |     |       |
| GCA | GAC | ACA | ATC | CGG | AAT | GCT | CAA | GCT | TCA | GGT | GAA | GGG | TTA | ACA | CAT | 10532 |
| Ala | Asp | Thr | Ile | Arg | Asn | Ala | Gln | Ala | Ser | Gly | Glu | Gly | Leu | Thr | His |       |
|     |     | 420 |     |     |     |     | 425 |     |     |     |     | 430 |     |     |     |       |
| GAG | CAG | TGC | GTT | GAT | AAC | TGG | AAA | TCT | TTT | GCT | GGA | GTG | AAA | TTT | GGC | 10580 |
| Glu | Gln | Cys | Val | Asp | Asn | Trp | Lys | Ser | Phe | Ala | Gly | Val | Lys | Phe | Gly |       |
|     |     | 435 |     |     |     |     | 440 |     |     |     |     | 445 |     |     |     |       |
| TGC | TTT | ATG | CCT | CTT | AGC | CTG | GAT | AGT | GAT | CTG | ACA | ATG | TAC | CTA | AAG | 10628 |
| Cys | Phe | Met | Pro | Leu | Ser | Leu | Asp | Ser | Asp | Leu | Thr | Met | Tyr | Leu | Lys |       |
| 450 |     |     |     |     | 455 |     |     |     |     | 460 |     |     |     |     | 465 |       |
| GAC | AAG | GCA | CTT | GCT | GCT | CTC | CAA | AGG | GAA | TGG | GAT | TCA | GTT | TAC | CCG | 10676 |
| Asp | Lys | Ala | Leu | Ala | Ala | Leu | Gln | Arg | Glu | Trp | Asp | Ser | Val | Tyr | Pro |       |

|     |     |     |     |     | 470 |     |     |     |     | 475 |     |     |     |     | 480 |     |       |
|-----|-----|-----|-----|-----|-----|-----|-----|-----|-----|-----|-----|-----|-----|-----|-----|-----|-------|
| AAA | GAG | TTC | CTG | CGT | TAC | GAC | CCT | CCC | AAG | GGA | ACC | GGG | TCA | CGG | AGG |     | 10724 |
| Lys | Glu | Phe | Leu | Arg | Tyr | Asp | Pro | Pro | Lys | Gly | Thr | Gly | Ser | Arg | Arg |     |       |
|     |     |     | 485 |     |     |     |     | 490 |     |     |     |     | 495 |     |     |     |       |

CTT GTA GAT GTT TTC CTT AAT GAT TCG AGC TTT GAC CCA TAT GAT GTG   10772
Leu Val Asp Val Phe Leu Asn Asp Ser Ser Phe Asp Pro Tyr Asp Val
        500             505             510

ATA ATG TAT GTT GTA AGT GGA GCT TAC CTC CAT GAC CCT GAG TTC AAC   10820
Ile Met Tyr Val Val Ser Gly Ala Tyr Leu His Asp Pro Glu Phe Asn
    515             520             525

CTG TCT TAC AGC CTG AAA GAA AAG GAG ATC AAG GAA ACA GGT AGA CTT   10868
Leu Ser Tyr Ser Leu Lys Glu Lys Glu Ile Lys Glu Thr Gly Arg Leu
530             535             540             545

TTT GCT AAA ATG ACT TAC AAA ATG AGG GCA TGC CAA GTG ATT GCT GAA   10916
Phe Ala Lys Met Thr Tyr Lys Met Arg Ala Cys Gln Val Ile Ala Glu
                550             555             560

AAT CTA ATC TCA AAC GGG ATT GGC AAA TAT TTT AAG GAC AAT GGG ATG   10964
Asn Leu Ile Ser Asn Gly Ile Gly Lys Tyr Phe Lys Asp Asn Gly Met
            565             570             575

GCC AAG GAT GAG CAC GAT TTG ACT AAG GCA CTC CAC ACT CTA GCT GTC   11012
Ala Lys Asp Glu His Asp Leu Thr Lys Ala Leu His Thr Leu Ala Val
        580             585             590

TCA GGA GTC CCC AAA GAT CTC AAA GAA AGT CAC AGG GGG GGG CCA GTC   11060
Ser Gly Val Pro Lys Asp Leu Lys Glu Ser His Arg Gly Gly Pro Val
595             600             605

TTA AAA ACC TAC TCC CGA AGC CCA GTC CAC ACA AGT ACC AGG AAC GTG   11108
Leu Lys Thr Tyr Ser Arg Ser Pro Val His Thr Ser Thr Arg Asn Val
610             615             620             625

AGA GCA GCA AAA GGG TTT ATA GGG TTC CCT CAA GTA ATT CGG CAG GAC   11156
Arg Ala Ala Lys Gly Phe Ile Gly Phe Pro Gln Val Ile Arg Gln Asp
                630             635             640

CAA GAC ACT GAT CAT CCG GAG AAT ATG GAA GCT TAC GAG ACA GTC AGT   11204
Gln Asp Thr Asp His Pro Glu Asn Met Glu Ala Tyr Glu Thr Val Ser
            645             650             655

GCA TTT ATC ACG ACT GAT CTC AAG AAG TAC TGC CTT AAT TGG AGA TAT   11252
Ala Phe Ile Thr Thr Asp Leu Lys Lys Tyr Cys Leu Asn Trp Arg Tyr
        660             665             670

GAG ACC ATC AGC TTG TTT GCA CAG AGG CTA AAT GAG ATT TAC GGA TTG   11300
Glu Thr Ile Ser Leu Phe Ala Gln Arg Leu Asn Glu Ile Tyr Gly Leu
675             680             685

CCC TCA TTT TTC CAG TGG CTG CAT AAG AGG CTT GAG ACC TCT GTC CTG   11348
Pro Ser Phe Phe Gln Trp Leu His Lys Arg Leu Glu Thr Ser Val Leu
690             695             700             705

TAT GTA AGT GAC CCT CAT TGC CCC CCC GAC CTT GAC GCC CAT ATC CCG   11396
Tyr Val Ser Asp Pro His Cys Pro Pro Asp Leu Asp Ala His Ile Pro
            710             715             720

TTA TAT AAA GTC CCC AAT GAT CAA ATC TTC ATT AAG TAC CCT ATG GGA   11444
Leu Tyr Lys Val Pro Asn Asp Gln Ile Phe Ile Lys Tyr Pro Met Gly
        725             730             735

GGT ATA GAA GGG TAT TGT CAG AAG CTG TGG ACC ATC AGC ACC ATT CCC   11492
Gly Ile Glu Gly Tyr Cys Gln Lys Leu Trp Thr Ile Ser Thr Ile Pro
        740             745             750

TAT CTA TAC CTG GCT GCT TAT GAG AGC GGA GTA AGG ATT GCT TCG TTA   11540
Tyr Leu Tyr Leu Ala Ala Tyr Glu Ser Gly Val Arg Ile Ala Ser Leu
755             760             765

GTG CAA GGG GAC AAT CAG ACC ATA GCC GTA ACA AAA AGG GTA CCC AGC   11588
Val Gln Gly Asp Asn Gln Thr Ile Ala Val Thr Lys Arg Val Pro Ser
770             775             780             785

ACA TGG CCC TAC AAC CTT AAG AAA CGG GAA GCT GCT AGA GTA ACT AGA   11636
Thr Trp Pro Tyr Asn Leu Lys Lys Arg Glu Ala Ala Arg Val Thr Arg

-continued

|  |  |  |  |  |  |  |  |  |  |  |  |  |  |  |  |
|---|---|---|---|---|---|---|---|---|---|---|---|---|---|---|---|
|  |  |  | 790 |  |  |  | 795 |  |  |  |  | 800 |  |  |  |
| GAT | TAC | TTT | GTA | ATT | CTT | AGG | CAA | AGG | CTA | CAT | GAT | ATT | GGC | CAT | CAC | 11684 |
| Asp | Tyr | Phe | Val | Ile | Leu | Arg | Gln | Arg | Leu | His | Asp | Ile | Gly | His | His |  |
|  |  |  | 805 |  |  |  | 810 |  |  |  |  | 815 |  |  |  |
| CTC | AAG | GCA | AAT | GAG | ACA | ATT | GTT | TCA | TCA | CAT | TTT | TTT | GTC | TAT | TCA | 11732 |
| Leu | Lys | Ala | Asn | Glu | Thr | Ile | Val | Ser | Ser | His | Phe | Phe | Val | Tyr | Ser |  |
|  |  |  | 820 |  |  |  | 825 |  |  |  |  | 830 |  |  |  |
| AAA | GGA | ATA | TAT | TAT | GAT | GGG | CTA | CTT | GTG | TCC | CAA | TCA | CTC | AAG | AGC | 11780 |
| Lys | Gly | Ile | Tyr | Tyr | Asp | Gly | Leu | Leu | Val | Ser | Gln | Ser | Leu | Lys | Ser |  |
|  |  |  | 835 |  |  |  | 840 |  |  |  |  | 845 |  |  |  |
| ATC | GCA | AGA | TGT | GTA | TTC | TGG | TCA | GAG | ACT | ATA | GTT | GAT | GAA | ACA | AGG | 11828 |
| Ile | Ala | Arg | Cys | Val | Phe | Trp | Ser | Glu | Thr | Ile | Val | Asp | Glu | Thr | Arg |  |
| 850 |  |  |  |  | 855 |  |  |  |  | 860 |  |  |  |  | 865 |  |
| GCA | GCA | TGC | AGT | AAT | ATT | GCT | ACA | ACA | ATG | GCT | AAA | AGC | ATC | GAG | AGA | 11876 |
| Ala | Ala | Cys | Ser | Asn | Ile | Ala | Thr | Thr | Met | Ala | Lys | Ser | Ile | Glu | Arg |  |
|  |  |  | 870 |  |  |  | 875 |  |  |  |  | 880 |  |  |  |
| GGT | TAT | GAC | CGT | TAC | CTT | GCA | TAT | TCC | CTG | AAC | GTC | CTA | AAA | GTG | ATA | 11924 |
| Gly | Tyr | Asp | Arg | Tyr | Leu | Ala | Tyr | Ser | Leu | Asn | Val | Leu | Lys | Val | Ile |  |
|  |  |  | 885 |  |  |  | 890 |  |  |  |  | 895 |  |  |  |
| CAG | CAA | ATT | CTG | ATC | TCT | CTT | GGC | TTC | ACA | ATC | AAT | TCA | ACC | ATG | ACC | 11972 |
| Gln | Gln | Ile | Leu | Ile | Ser | Leu | Gly | Phe | Thr | Ile | Asn | Ser | Thr | Met | Thr |  |
|  |  | 900 |  |  |  |  | 905 |  |  |  |  | 910 |  |  |  |
| CGG | GAT | GTA | GTC | ATA | CCC | CTC | CTC | ACA | AAC | AAC | GAC | CTC | TTA | ATA | AGG | 12020 |
| Arg | Asp | Val | Val | Ile | Pro | Leu | Leu | Thr | Asn | Asn | Asp | Leu | Leu | Ile | Arg |  |
|  |  | 915 |  |  |  |  | 920 |  |  |  |  | 925 |  |  |  |
| ATG | GCA | CTG | TTG | CCC | GCT | CCT | ATT | GGG | GGG | ATG | AAT | TAT | CTG | AAT | ATG | 12068 |
| Met | Ala | Leu | Leu | Pro | Ala | Pro | Ile | Gly | Gly | Met | Asn | Tyr | Leu | Asn | Met |  |
| 930 |  |  |  |  | 935 |  |  |  |  | 940 |  |  |  |  | 945 |  |
| AGC | AGG | CTG | TTT | GTC | AGA | AAC | ATC | GGT | GAT | CCA | GTA | ACA | TCA | TCA | ATT | 12116 |
| Ser | Arg | Leu | Phe | Val | Arg | Asn | Ile | Gly | Asp | Pro | Val | Thr | Ser | Ser | Ile |  |
|  |  |  | 950 |  |  |  | 955 |  |  |  |  | 960 |  |  |  |
| GCT | GAT | CTC | AAG | AGA | ATG | ATT | CTC | GCC | TCA | CTA | ATG | CCT | GAA | GAG | ACC | 12164 |
| Ala | Asp | Leu | Lys | Arg | Met | Ile | Leu | Ala | Ser | Leu | Met | Pro | Glu | Glu | Thr |  |
|  |  |  | 965 |  |  |  | 970 |  |  |  |  | 975 |  |  |  |
| CTC | CAT | CAA | GTA | ATG | ACA | CAA | CAA | CCG | GGG | GAC | TCT | TCA | TTC | CTA | GAC | 12212 |
| Leu | His | Gln | Val | Met | Thr | Gln | Gln | Pro | Gly | Asp | Ser | Ser | Phe | Leu | Asp |  |
|  |  | 980 |  |  |  |  | 985 |  |  |  |  | 990 |  |  |  |
| TGG | GCT | AGC | GAC | CCT | TAC | TCA | GCA | AAT | CTT | GTA | TGT | GTC | CAG | AGC | ATC | 12260 |
| Trp | Ala | Ser | Asp | Pro | Tyr | Ser | Ala | Asn | Leu | Val | Cys | Val | Gln | Ser | Ile |  |
| 995 |  |  |  |  | 1000 |  |  |  |  | 1005 |  |  |  |  |  |  |
| ACT | AGA | CTC | CTC | AAG | AAC | ATA | ACT | GCA | AGG | TTT | GTC | CTG | ATC | CAT | AGT | 12308 |
| Thr | Arg | Leu | Leu | Lys | Asn | Ile | Thr | Ala | Arg | Phe | Val | Leu | Ile | His | Ser |  |
| 1010 |  |  |  |  | 1015 |  |  |  |  | 1020 |  |  |  |  | 1025 |  |
| CCA | AAC | CCA | ATG | TTA | AAA | GGA | TTA | TTC | CAT | GAT | GAC | AGT | AAA | GAA | GAG | 12356 |
| Pro | Asn | Pro | Met | Leu | Lys | Gly | Leu | Phe | His | Asp | Asp | Ser | Lys | Glu | Glu |  |
|  |  |  |  | 1030 |  |  |  |  | 1035 |  |  |  |  | 1040 |  |  |
| GAC | GAG | GGA | CTG | GCG | GCA | TTC | CTC | ATG | GAC | AGG | CAT | ATT | ATA | GTA | CCT | 12404 |
| Asp | Glu | Gly | Leu | Ala | Ala | Phe | Leu | Met | Asp | Arg | His | Ile | Ile | Val | Pro |  |
|  |  |  | 1045 |  |  |  | 1050 |  |  |  |  | 1055 |  |  |  |
| AGG | GCA | GCT | CAT | GAA | ATC | CTG | GAT | CAT | AGT | GTC | ACA | GGG | GCA | AGA | GAG | 12452 |
| Arg | Ala | Ala | His | Glu | Ile | Leu | Asp | His | Ser | Val | Thr | Gly | Ala | Arg | Glu |  |
|  |  |  | 1060 |  |  |  | 1065 |  |  |  |  | 1070 |  |  |  |
| TCT | ATT | GCA | GGC | ATG | CTG | GAT | ACC | ACA | AAA | GGC | CTG | ATT | CGA | GCC | AGC | 12500 |
| Ser | Ile | Ala | Gly | Met | Leu | Asp | Thr | Thr | Lys | Gly | Leu | Ile | Arg | Ala | Ser |  |
|  |  |  | 1075 |  |  |  | 1080 |  |  |  |  | 1085 |  |  |  |
| ATG | AGG | AAG | GGG | GGG | TTA | ACC | TCT | CGA | GTG | ATA | ACC | AGA | TTG | TCC | AAT | 12548 |
| Met | Arg | Lys | Gly | Gly | Leu | Thr | Ser | Arg | Val | Ile | Thr | Arg | Leu | Ser | Asn |  |
| 1090 |  |  |  |  | 1095 |  |  |  |  | 1100 |  |  |  |  | 1105 |  |
| TAT | GAC | TAT | GAA | CAA | TTC | AGA | GCA | GGG | ATG | GTG | CTA | TTG | ACG | GGA | AGA | 12596 |
| Tyr | Asp | Tyr | Glu | Gln | Phe | Arg | Ala | Gly | Met | Val | Leu | Leu | Thr | Gly | Arg |  |

```
                       1110                           1115                            1120
AAG  AGA  AAT  GTC  CTC  ATT  GAC  AAA  GAG  TCA  TGT  TCA  GTG  CAG  CTG  GCG            12644
Lys  Arg  Asn  Val  Leu  Ile  Asp  Lys  Glu  Ser  Cys  Ser  Val  Gln  Leu  Ala
               1125                         1130                          1135

AGA  GCT  CTA  AGA  AGC  CAT  ATG  TGG  GCG  AGG  CTA  GCT  CGA  GGA  CGG  CCT            12692
Arg  Ala  Leu  Arg  Ser  His  Met  Trp  Ala  Arg  Leu  Ala  Arg  Gly  Arg  Pro
               1140                         1145                          1150

ATT  TAC  GGC  CTT  GAG  GTC  CCT  GAT  GTA  CTA  GAA  TCT  ATG  CGA  GGC  CAC            12740
Ile  Tyr  Gly  Leu  Glu  Val  Pro  Asp  Val  Leu  Glu  Ser  Met  Arg  Gly  His
     1155                          1160                         1165

CTT  ATT  CGG  CGT  CAT  GAG  ACA  TGT  GTC  ATC  TGC  GAG  TGT  GGA  TCA  GTC            12788
Leu  Ile  Arg  Arg  His  Glu  Thr  Cys  Val  Ile  Cys  Glu  Cys  Gly  Ser  Val
1170                     1175                         1180                     1185

AAC  TAC  GGA  TGG  TTT  TTT  GTC  CCC  TCG  GGT  TGC  CAA  CTG  GAT  GAT  ATT            12836
Asn  Tyr  Gly  Trp  Phe  Phe  Val  Pro  Ser  Gly  Cys  Gln  Leu  Asp  Asp  Ile
                         1190                         1195                     1200

GAC  AAG  GAA  ACA  TCA  TCC  TTG  AGA  GTC  CCA  TAT  ATT  GGT  TCT  ACC  ACT            12884
Asp  Lys  Glu  Thr  Ser  Ser  Leu  Arg  Val  Pro  Tyr  Ile  Gly  Ser  Thr  Thr
                         1205                         1210                     1215

GAT  GAG  AGA  ACA  GAC  ATG  AAG  CTT  GCC  TTC  GTA  AGA  GCC  CCA  AGT  CGA            12932
Asp  Glu  Arg  Thr  Asp  Met  Lys  Leu  Ala  Phe  Val  Arg  Ala  Pro  Ser  Arg
               1220                         1225                          1230

TCC  TTG  CGA  TCT  GCT  GTT  AGA  ATA  GCA  ACA  GTG  TAC  TCA  TGG  GCT  TAC            12980
Ser  Leu  Arg  Ser  Ala  Val  Arg  Ile  Ala  Thr  Val  Tyr  Ser  Trp  Ala  Tyr
     1235                          1240                         1245

GGT  GAT  GAT  GAT  AGC  TCT  TGG  AAC  GAA  GCC  TGG  TTG  TTG  GCT  AGG  CAA            13028
Gly  Asp  Asp  Asp  Ser  Ser  Trp  Asn  Glu  Ala  Trp  Leu  Leu  Ala  Arg  Gln
1250                     1255                         1260                     1265

AGG  GCC  AAT  GTG  AGC  CTG  GAG  GAG  CTA  AGG  GTG  ATC  ACT  CCC  ATC  TCA            13076
Arg  Ala  Asn  Val  Ser  Leu  Glu  Glu  Leu  Arg  Val  Ile  Thr  Pro  Ile  Ser
                         1270                         1275                     1280

ACT  TCG  ACT  AAT  TTA  GCG  CAT  AGG  TTG  AGG  GAT  CGT  AGC  ACT  CAA  GTG            13124
Thr  Ser  Thr  Asn  Leu  Ala  His  Arg  Leu  Arg  Asp  Arg  Ser  Thr  Gln  Val
                         1285                         1290                     1295

AAA  TAC  TCA  GGT  ACA  TCC  CTT  GTC  CGA  GTG  GCG  AGG  TAT  ACC  ACA  ATC            13172
Lys  Tyr  Ser  Gly  Thr  Ser  Leu  Val  Arg  Val  Ala  Arg  Tyr  Thr  Thr  Ile
               1300                         1305                          1310

TCC  AAC  GAC  AAT  CTC  TCA  TTT  GTC  ATA  TCA  GAT  AAG  AAG  GTT  GAT  ACT            13220
Ser  Asn  Asp  Asn  Leu  Ser  Phe  Val  Ile  Ser  Asp  Lys  Lys  Val  Asp  Thr
               1315                         1320                          1325

AAC  TTT  ATA  TAC  CAA  CAA  GGA  ATG  CTT  CTA  GGG  TTG  GGT  GTT  TTA  GAA            13268
Asn  Phe  Ile  Tyr  Gln  Gln  Gly  Met  Leu  Leu  Gly  Leu  Gly  Val  Leu  Glu
1330                     1335                         1340                     1345

ACA  TTG  TTT  CGA  CTC  GAG  AAA  GAT  ACC  GGA  TCA  TCT  AAC  ACG  GTA  TTA            13316
Thr  Leu  Phe  Arg  Leu  Glu  Lys  Asp  Thr  Gly  Ser  Ser  Asn  Thr  Val  Leu
                         1350                         1355                     1360

CAT  CTT  CAC  GTC  GAA  ACA  GAT  TGT  TGC  GTG  ATC  CCG  ATG  ATA  GAT  CAT            13364
His  Leu  His  Val  Glu  Thr  Asp  Cys  Cys  Val  Ile  Pro  Met  Ile  Asp  His
                    1365                         1370                     1375

CCC  AGG  ATA  CCC  AGC  TCC  CGC  AAG  CTA  GAG  CTG  AGG  GCA  GAG  CTA  TGT            13412
Pro  Arg  Ile  Pro  Ser  Ser  Arg  Lys  Leu  Glu  Leu  Arg  Ala  Glu  Leu  Cys
               1380                         1385                          1390

ACC  AAC  CCA  TTG  ATA  TAT  GAT  AAT  GCA  CCT  TTA  ATT  GAC  AGA  GAT  ACA            13460
Thr  Asn  Pro  Leu  Ile  Tyr  Asp  Asn  Ala  Pro  Leu  Ile  Asp  Arg  Asp  Thr
               1395                         1400                          1405

ACA  AGG  CTA  TAC  ACC  CAG  AGC  CAT  AGG  AGG  CAC  CTT  GTG  GAA  TTT  GTT            13508
Thr  Arg  Leu  Tyr  Thr  Gln  Ser  His  Arg  Arg  His  Leu  Val  Glu  Phe  Val
1410                     1415                         1420                     1425

ACA  TGG  TCC  ACA  CCC  CAA  CTA  TAT  CAC  ATT  TTA  GCT  AAG  TCC  ACA  GCA            13556
Thr  Trp  Ser  Thr  Pro  Gln  Leu  Tyr  His  Ile  Leu  Ala  Lys  Ser  Thr  Ala
```

-continued

|     |     |     |     |     |     |     |     |     |     |     |     |     |     |     |     |       |
|-----|-----|-----|-----|-----|-----|-----|-----|-----|-----|-----|-----|-----|-----|-----|-----|-------|
|     |     |     |     | 1430 |     |     |     |     | 1435 |     |     |     |     | 1440 |     |       |
| CTA | TCT | ATG | ATT | GAC | CTG | GTA | ACA | AAA | TTT | GAG | AAG | GAC | CAT | ATG | AAT | 13604 |
| Leu | Ser | Met | Ile | Asp | Leu | Val | Thr | Lys | Phe | Glu | Lys | Asp | His | Met | Asn |       |
|     |     |     | 1445 |     |     |     |     | 1450 |     |     |     |     | 1455 |     |     |       |
| GAA | ATT | TCA | GCT | CTC | ATA | GGG | GAT | GAC | GAT | ATC | AAT | AGT | TTC | ATA | ACT | 13652 |
| Glu | Ile | Ser | Ala | Leu | Ile | Gly | Asp | Asp | Asp | Ile | Asn | Ser | Phe | Ile | Thr |       |
|     |     | 1460 |     |     |     |     | 1465 |     |     |     |     | 1470 |     |     |     |       |
| GAG | TTT | CTC | GTC | ATA | GAG | CCA | AGA | TTA | TTC | ACT | ATC | TAC | TTG | GGC | CAG | 13700 |
| Glu | Phe | Leu | Val | Ile | Glu | Pro | Arg | Leu | Phe | Thr | Ile | Tyr | Leu | Gly | Gln |       |
|     | 1475 |     |     |     |     | 1480 |     |     |     |     | 1485 |     |     |     |     |       |
| TGT | GCG | GCC | ATC | AAT | TGG | GCA | TTT | GAT | GTA | CAT | TAT | CAT | AGA | CCA | TCA | 13748 |
| Cys | Ala | Ala | Ile | Asn | Trp | Ala | Phe | Asp | Val | His | Tyr | His | Arg | Pro | Ser |       |
| 1490 |     |     |     |     | 1495 |     |     |     |     | 1500 |     |     |     |     | 1505 |       |
| GGG | AAA | TAT | CAG | ATG | GGT | GAG | CTG | TTG | TCA | TCG | TTC | CTT | TCT | AGA | ATG | 13796 |
| Gly | Lys | Tyr | Gln | Met | Gly | Glu | Leu | Leu | Ser | Ser | Phe | Leu | Ser | Arg | Met |       |
|     |     |     |     | 1510 |     |     |     |     | 1515 |     |     |     |     | 1520 |     |       |
| AGC | AAA | GGA | GTG | TTT | AAG | GTG | CTT | GTC | AAT | GCT | CTA | AGC | CAC | CCA | AAG | 13844 |
| Ser | Lys | Gly | Val | Phe | Lys | Val | Leu | Val | Asn | Ala | Leu | Ser | His | Pro | Lys |       |
|     |     |     | 1525 |     |     |     |     | 1530 |     |     |     |     | 1535 |     |     |       |
| ATC | TAC | AAG | AAA | TTC | TGG | CAT | TGT | GGT | ATT | ATA | GAG | CCT | ATC | CAT | GGT | 13892 |
| Ile | Tyr | Lys | Lys | Phe | Trp | His | Cys | Gly | Ile | Ile | Glu | Pro | Ile | His | Gly |       |
|     |     | 1540 |     |     |     |     | 1545 |     |     |     |     | 1550 |     |     |     |       |
| CCT | TCA | CTT | GAT | GCT | CAA | AAC | TTG | CAC | ACA | ACT | GTC | TGC | AAC | ATG | GTT | 13940 |
| Pro | Ser | Leu | Asp | Ala | Gln | Asn | Leu | His | Thr | Thr | Val | Cys | Asn | Met | Val |       |
|     | 1555 |     |     |     |     | 1560 |     |     |     |     | 1565 |     |     |     |     |       |
| TAC | ACA | TGC | TAT | ATG | ACC | TAC | CTC | GAC | CTG | TTG | TTG | AAT | GAA | GAG | TTA | 13988 |
| Tyr | Thr | Cys | Tyr | Met | Thr | Tyr | Leu | Asp | Leu | Leu | Leu | Asn | Glu | Glu | Leu |       |
| 1570 |     |     |     |     | 1575 |     |     |     |     | 1580 |     |     |     |     | 1585 |       |
| GAA | GAG | TTC | ACA | TTT | CTC | TTG | TGT | GAA | AGC | GAC | GAG | GAT | GTA | GTA | CCG | 14036 |
| Glu | Glu | Phe | Thr | Phe | Leu | Leu | Cys | Glu | Ser | Asp | Glu | Asp | Val | Val | Pro |       |
|     |     |     |     | 1590 |     |     |     |     | 1595 |     |     |     |     | 1600 |     |       |
| GAC | AGA | TTC | GAC | AAC | ATC | CAG | GCA | AAA | CAC | TTA | TGT | GTT | CTG | GCA | GAT | 14084 |
| Asp | Arg | Phe | Asp | Asn | Ile | Gln | Ala | Lys | His | Leu | Cys | Val | Leu | Ala | Asp |       |
|     |     |     | 1605 |     |     |     |     | 1610 |     |     |     |     | 1615 |     |     |       |
| TTG | TAC | TGT | CAA | CCA | GGG | GCC | TGC | CCA | CCA | ATT | CGA | GGT | CTA | AGA | CCG | 14132 |
| Leu | Tyr | Cys | Gln | Pro | Gly | Ala | Cys | Pro | Pro | Ile | Arg | Gly | Leu | Arg | Pro |       |
|     |     | 1620 |     |     |     |     | 1625 |     |     |     |     | 1630 |     |     |     |       |
| GTA | GAG | AAA | TGT | GCA | GTT | CTA | ACC | GAC | CAT | ATC | AAG | GCA | GAG | GCT | AGG | 14180 |
| Val | Glu | Lys | Cys | Ala | Val | Leu | Thr | Asp | His | Ile | Lys | Ala | Glu | Ala | Arg |       |
|     | 1635 |     |     |     |     | 1640 |     |     |     |     | 1645 |     |     |     |     |       |
| TTA | TCT | CCA | GCA | GGA | TCT | TCG | TGG | AAC | ATA | AAT | CCA | ATT | ATT | GTA | GAC | 14228 |
| Leu | Ser | Pro | Ala | Gly | Ser | Ser | Trp | Asn | Ile | Asn | Pro | Ile | Ile | Val | Asp |       |
| 1650 |     |     |     |     | 1655 |     |     |     |     | 1660 |     |     |     |     | 1665 |       |
| CAT | TAC | TCA | TGC | TCT | CTG | ACT | TAT | CTC | CGG | CGA | GGA | TCG | ATC | AAA | CAG | 14276 |
| His | Tyr | Ser | Cys | Ser | Leu | Thr | Tyr | Leu | Arg | Arg | Gly | Ser | Ile | Lys | Gln |       |
|     |     |     |     | 1670 |     |     |     |     | 1675 |     |     |     |     | 1680 |     |       |
| ATA | AGA | TTG | AGA | GTT | GAT | CCA | GGA | TTC | ATT | TTC | GAC | GCC | CTC | GCT | GAG | 14324 |
| Ile | Arg | Leu | Arg | Val | Asp | Pro | Gly | Phe | Ile | Phe | Asp | Ala | Leu | Ala | Glu |       |
|     |     |     | 1685 |     |     |     |     | 1690 |     |     |     |     | 1695 |     |     |       |
| GTA | AAT | GTC | AGT | CAG | CCA | AAG | ATC | GGC | AGC | AAC | AAC | ATC | TCA | AAT | ATG | 14372 |
| Val | Asn | Val | Ser | Gln | Pro | Lys | Ile | Gly | Ser | Asn | Asn | Ile | Ser | Asn | Met |       |
|     |     | 1700 |     |     |     |     | 1705 |     |     |     |     | 1710 |     |     |     |       |
| AGC | ATC | AAG | GCT | TTC | AGA | CCC | CCA | CAC | GAT | GAT | GTT | GCA | AAA | TTG | CTC | 14420 |
| Ser | Ile | Lys | Ala | Phe | Arg | Pro | Pro | His | Asp | Asp | Val | Ala | Lys | Leu | Leu |       |
|     | 1715 |     |     |     |     | 1720 |     |     |     |     | 1725 |     |     |     |     |       |
| AAA | GAT | ATC | AAC | ACA | AGC | AAG | CAC | AAT | CTT | CCC | ATT | TCA | GGG | GGC | AAT | 14468 |
| Lys | Asp | Ile | Asn | Thr | Ser | Lys | His | Asn | Leu | Pro | Ile | Ser | Gly | Gly | Asn |       |
| 1730 |     |     |     |     | 1735 |     |     |     |     | 1740 |     |     |     |     | 1745 |       |
| CTC | GCC | AAT | TAT | GAA | ATC | CAT | GCT | TTC | CGC | AGA | ATC | GGG | TTG | AAC | TCA | 14516 |
| Leu | Ala | Asn | Tyr | Glu | Ile | His | Ala | Phe | Arg | Arg | Ile | Gly | Leu | Asn | Ser |       |

-continued

```
            1750                    1755                    1760
TCT GCT TGC TAC AAA GCT GTT GAG ATA TCA ACA TTA ATT AGG AGA TGC        14564
Ser Ala Cys Tyr Lys Ala Val Glu Ile Ser Thr Leu Ile Arg Arg Cys
            1765                    1770                    1775

CTT GAG CCA GGG GAG GAC GGC TTG TTC TTG GGT GAG GGA TCG GGT TCT        14612
Leu Glu Pro Gly Glu Asp Gly Leu Phe Leu Gly Glu Gly Ser Gly Ser
            1780                    1785                    1790

ATG TTG ATC ACT TAT AAG GAG ATA CTT AAA CTA AAC AAG TGC TTC TAT        14660
Met Leu Ile Thr Tyr Lys Glu Ile Leu Lys Leu Asn Lys Cys Phe Tyr
            1795                    1800                    1805

AAT AGT GGG GTT TCC GCC AAT TCT AGA TCT GGT CAA AGG GAA TTA GCA        14708
Asn Ser Gly Val Ser Ala Asn Ser Arg Ser Gly Gln Arg Glu Leu Ala
1810                    1815                    1820                    1825

CCC TAT CCC TCC GAA GTT GGC CTT GTC GAA CAC AGA ATG GGA GTA GGT        14756
Pro Tyr Pro Ser Glu Val Gly Leu Val Glu His Arg Met Gly Val Gly
                        1830                    1835                    1840

AAT ATT GTC AAA GTG CTC TTT AAC GGG AGG CCC GAA GTC ACG TGG GTA        14804
Asn Ile Val Lys Val Leu Phe Asn Gly Arg Pro Glu Val Thr Trp Val
            1845                    1850                    1855

GGC AGT GTA GAT TGC TTC AAT TTC ATA GTT AGT AAT ATC CCT ACC TCT        14852
Gly Ser Val Asp Cys Phe Asn Phe Ile Val Ser Asn Ile Pro Thr Ser
            1860                    1865                    1870

AGT GTG GGG TTT ATC CAT TCA GAT ATA GAG ACC TTG CCT AAC AAA GAT        14900
Ser Val Gly Phe Ile His Ser Asp Ile Glu Thr Leu Pro Asn Lys Asp
1875                    1880                    1885

ACT ATA GAG AAG CTA GAG GAA TTG GCA GCC ATC TTA TCG ATG GCT CTG        14948
Thr Ile Glu Lys Leu Glu Glu Leu Ala Ala Ile Leu Ser Met Ala Leu
1890                    1895                    1900                    1905

CTC CTG GGC AAA ATA GGA TCA ATA CTG GTG ATT AAG CTT ATG CCT TTC        14996
Leu Leu Gly Lys Ile Gly Ser Ile Leu Val Ile Lys Leu Met Pro Phe
            1910                    1915                    1920

AGC GGG GAT TTT GTT CAG GGA TTT ATA AGT TAT GTA GGG TCT TAT TAT        15044
Ser Gly Asp Phe Val Gln Gly Phe Ile Ser Tyr Val Gly Ser Tyr Tyr
            1925                    1930                    1935

AGA GAA GTG AAC CTT GTA TAC CCT AGA TAC AGC AAC TTC ATA TCT ACT        15092
Arg Glu Val Asn Leu Val Tyr Pro Arg Tyr Ser Asn Phe Ile Ser Thr
            1940                    1945                    1950

GAA TCT TAT TTG GTT ATG ACA GAT CTC AAG GCT AAC CGG CTA ATG AAT        15140
Glu Ser Tyr Leu Val Met Thr Asp Leu Lys Ala Asn Arg Leu Met Asn
            1955                    1960                    1965

CCT GAA AAG ATT AAG CAG CAG ATA ATT GAA TCA TCT GTG AGG ACT TCA        15188
Pro Glu Lys Ile Lys Gln Gln Ile Ile Glu Ser Ser Val Arg Thr Ser
1970                    1975                    1980                    1985

CCT GGA CTT ATA GGT CAC ATC CTA TCC ATT AAG CAA CTA AGC TGC ATA        15236
Pro Gly Leu Ile Gly His Ile Leu Ser Ile Lys Gln Leu Ser Cys Ile
            1990                    1995                    2000

CAA GCA ATT GTG GGA GAC GTA GTT AGT AGA GGT GAT ATC AAT CCT ACT        15284
Gln Ala Ile Val Gly Asp Val Val Ser Arg Gly Asp Ile Asn Pro Thr
            2005                    2010                    2015

CTG AAA AAA CTT ACA CCT ATA GAG CAG GTG CTG ATC AAT TGC GGG TTG        15332
Leu Lys Lys Leu Thr Pro Ile Glu Gln Val Leu Ile Asn Cys Gly Leu
            2020                    2025                    2030

GCA ATT AAC GGA CCT AAG CTG TGC AAA GAA TTG ATC CAC CAT GAT GTT        15380
Ala Ile Asn Gly Pro Lys Leu Cys Lys Glu Leu Ile His His Asp Val
            2035                    2040                    2045

GCC TCA GGG CAA GAT GGA TTG CTT AAT TCT ATC CTC ATC CTC TAC AGG        15428
Ala Ser Gly Gln Asp Gly Leu Leu Asn Ser Ile Leu Ile Leu Tyr Arg
            2050                    2055                    2060                    2065

GAG TTG GCA AGA TTC AAA GAC AAC CGA AGA AGT CAA CAA GGG ATG TTC        15476
Glu Leu Ala Arg Phe Lys Asp Asn Arg Arg Ser Gln Gln Gly Met Phe
```

-continued

```
                   2070                        2075                          2080
CAC  GCT  TAC  CCC  GTA  TTG  GTA  AGT  AGC  AGG  CAA  CGA  GAA  CTT  ATA  TCT       15524
His  Ala  Tyr  Pro  Val  Leu  Val  Ser  Ser  Arg  Gln  Arg  Glu  Leu  Ile  Ser
               2085                      2090                      2095

AGG  ATC  ACC  CGC  AAA  TTT  TGG  GGG  CAC  ATT  CTT  CTT  TAC  TCC  GGG  AAC       15572
Arg  Ile  Thr  Arg  Lys  Phe  Trp  Gly  His  Ile  Leu  Leu  Tyr  Ser  Gly  Asn
               2100                      2105                      2110

AGA  AAG  TTG  ATA  AAT  AAG  TTT  ATC  CAG  AAT  CTC  AAG  TCC  GGC  TAT  CTG       15620
Arg  Lys  Leu  Ile  Asn  Lys  Phe  Ile  Gln  Asn  Leu  Lys  Ser  Gly  Tyr  Leu
               2115                      2120                      2125

ATA  CTA  GAC  TTA  CAC  CAG  AAT  ATC  TTC  GTT  AAG  AAT  CTA  TCC  AAG  TCA       15668
Ile  Leu  Asp  Leu  His  Gln  Asn  Ile  Phe  Val  Lys  Asn  Leu  Ser  Lys  Ser
2130                2135                      2140                      2145

GAG  AAA  CAG  ATT  ATT  ATG  ACG  GGG  GGT  TTG  AAA  CGT  GAG  TGG  GTT  TTT       15716
Glu  Lys  Gln  Ile  Ile  Met  Thr  Gly  Gly  Leu  Lys  Arg  Glu  Trp  Val  Phe
               2150                      2155                      2160

AAG  GTA  ACA  GTC  AAG  GAG  ACC  AAA  GAA  TGG  TAT  AAG  TTA  GTC  GGA  TAC       15764
Lys  Val  Thr  Val  Lys  Glu  Thr  Lys  Glu  Trp  Tyr  Lys  Leu  Val  Gly  Tyr
               2165                      2170                      2175

AGT  GCC  CTG  ATT  AAG  GAC  TAATTGGTTG  AACTCCGGAA  CCCTAATCCT                     15812
Ser  Ala  Leu  Ile  Lys  Asp
               2180

GCCCTAGGTG  GTTAGGCATT  ATTTGCAATA  TATTAAAGAA  AACTTTGAAA  ATACGAAGTT               15872

TCTATTCCCA  GCTTTGTCTG  GT                                                           15894
```

(2) INFORMATION FOR SEQ ID NO:2:

(i) SEQUENCE CHARACTERISTICS:
        (A) LENGTH: 525 amino acids
        (B) TYPE: amino acid
        (D) TOPOLOGY: linear (ii) MOLECULE TYPE: protein (xi) SEQUENCE DESCRIPTION: SEQ ID NO:2:

```
Met  Ala  Thr  Leu  Leu  Arg  Ser  Leu  Ala  Leu  Phe  Lys  Arg  Asn  Lys  Asp
 1                   5                        10                       15

Lys  Pro  Pro  Ile  Thr  Ser  Gly  Ser  Gly  Gly  Ala  Ile  Arg  Gly  Ile  Lys
               20                       25                       30

His  Ile  Ile  Ile  Val  Pro  Ile  Pro  Gly  Asp  Ser  Ser  Ile  Thr  Thr  Arg
          35                       40                       45

Ser  Arg  Leu  Leu  Asp  Arg  Leu  Val  Arg  Leu  Ile  Gly  Asn  Pro  Asp  Val
     50                       55                       60

Ser  Gly  Pro  Lys  Leu  Thr  Gly  Ala  Leu  Ile  Gly  Ile  Leu  Ser  Leu  Phe
65                       70                       75                       80

Val  Glu  Ser  Pro  Gly  Gln  Leu  Ile  Gln  Arg  Ile  Thr  Asp  Asp  Pro  Asp
                    85                       90                       95

Val  Ser  Ile  Arg  Leu  Leu  Glu  Val  Val  Gln  Ser  Asp  Gln  Ser  Gln  Ser
               100                      105                      110

Gly  Leu  Thr  Phe  Ala  Ser  Arg  Gly  Thr  Asn  Met  Glu  Asp  Glu  Ala  Asp
               115                      120                      125

Lys  Tyr  Phe  Ser  His  Asp  Pro  Ile  Ser  Ser  Asp  Gln  Ser  Arg  Phe
     130                      135                      140

Gly  Trp  Phe  Glu  Asn  Lys  Glu  Ile  Ser  Asp  Ile  Glu  Val  Gln  Asp  Pro
145                      150                      155                      160

Glu  Gly  Phe  Asn  Met  Ile  Leu  Gly  Thr  Ile  Leu  Ala  Gln  Ile  Trp  Val
                    165                      170                      175

Leu  Leu  Ala  Lys  Ala  Val  Thr  Ala  Pro  Asp  Thr  Ala  Ala  Asp  Ser  Glu
```

```
                              180                    185                      190
Leu  Arg  Arg  Trp  Ile  Lys  Tyr  Thr  Gln  Gln  Arg  Arg  Val  Gly  Glu
          195                      200                 205

Phe  Arg  Leu  Glu  Arg  Lys  Trp  Leu  Asp  Val  Val  Arg  Asn  Arg  Ile  Ala
     210                      215                      220

Glu  Asp  Leu  Ser  Leu  Arg  Arg  Phe  Met  Val  Ala  Leu  Ile  Leu  Asp  Ile
225                           230                 235                           240

Lys  Arg  Thr  Pro  Gly  Asn  Lys  Pro  Arg  Ile  Ala  Glu  Met  Ile  Cys  Asp
                    245                      250                           255

Ile  Asp  Thr  Tyr  Ile  Val  Glu  Ala  Gly  Leu  Ala  Ser  Phe  Ile  Leu  Thr
               260                      265                      270

Ile  Lys  Phe  Gly  Ile  Glu  Thr  Met  Tyr  Pro  Ala  Leu  Gly  Leu  His  Glu
          275                      280                      285

Phe  Ala  Gly  Glu  Leu  Ser  Thr  Leu  Glu  Ser  Leu  Met  Asn  Leu  Tyr  Gln
     290                      295                      300

Gln  Met  Gly  Glu  Thr  Ala  Pro  Tyr  Met  Val  Asn  Leu  Glu  Asn  Ser  Ile
305                           310                 315                           320

Gln  Asn  Lys  Phe  Ser  Ala  Gly  Ser  Tyr  Pro  Leu  Leu  Trp  Ser  Tyr  Ala
                    325                      330                      335

Met  Gly  Val  Gly  Val  Glu  Leu  Glu  Asn  Ser  Met  Gly  Gly  Leu  Asn  Phe
               340                      345                      350

Gly  Arg  Ser  Tyr  Phe  Asp  Pro  Ala  Tyr  Phe  Arg  Leu  Gly  Gln  Glu  Met
          355                      360                      365

Val  Arg  Arg  Ser  Ala  Gly  Lys  Val  Ser  Ser  Thr  Leu  Ala  Ser  Glu  Leu
     370                      375                      380

Gly  Ile  Thr  Ala  Glu  Asp  Ala  Arg  Leu  Val  Ser  Glu  Ile  Ala  Met  His
385                           390                 395                           400

Thr  Thr  Glu  Asp  Lys  Ile  Ser  Arg  Ala  Val  Gly  Pro  Arg  Gln  Ala  Gln
                    405                      410                           415

Val  Ser  Phe  Leu  His  Gly  Asp  Gln  Ser  Glu  Asn  Glu  Leu  Pro  Arg  Leu
               420                      425                      430

Gly  Gly  Lys  Glu  Asp  Arg  Arg  Val  Lys  Gln  Ser  Arg  Gly  Glu  Ala  Arg
          435                      440                      445

Glu  Ser  Tyr  Arg  Glu  Thr  Gly  Pro  Ser  Arg  Ala  Ser  Asp  Ala  Arg  Ala
     450                      455                      460

Ala  His  Leu  Pro  Thr  Gly  Thr  Pro  Leu  Asp  Ile  Asp  Thr  Ala  Ser  Glu
465                           470                 475                           480

Ser  Ser  Gln  Asp  Pro  Gln  Asp  Ser  Arg  Arg  Ser  Ala  Asp  Ala  Leu  Leu
                    485                      490                           495

Arg  Leu  Gln  Ala  Met  Ala  Gly  Ile  Ser  Glu  Glu  Gln  Gly  Ser  Asp  Thr
               500                      505                      510

Asp  Thr  Pro  Ile  Val  Tyr  Asn  Asp  Arg  Asn  Leu  Leu  Asp
               515                      520                 525
```

(2) INFORMATION FOR SEQ ID NO:3:

(i) SEQUENCE CHARACTERISTICS:
        (A) LENGTH: 507 amino acids
        (B) TYPE: amino acid
        (D) TOPOLOGY: linear (ii) MOLECULE TYPE: protein (xi) SEQUENCE DESCRIPTION: SEQ ID NO:3:

```
Met  Ala  Glu  Glu  Gln  Ala  Arg  His  Val  Lys  Asn  Gly  Leu  Glu  Cys  Ile
1                   5                        10                           15
```

-continued

```
Arg Ala Leu Lys Ala Glu Pro Ile Gly Ser Leu Ala Ile Glu Glu Ala
             20                  25                  30

Met Ala Ala Trp Ser Glu Ile Ser Asp Asn Pro Gly Gln Glu Arg Ala
             35                  40                  45

Thr Cys Arg Glu Glu Lys Ala Gly Ser Ser Gly Leu Ser Lys Pro Cys
         50                  55                  60

Leu Ser Ala Ile Gly Ser Thr Glu Gly Ala Pro Arg Ile Arg Gly
 65                  70                  75                  80

Gln Gly Pro Gly Glu Ser Asp Asp Ala Glu Thr Leu Gly Ile Pro
                     85                  90                  95

Pro Arg Asn Leu Gln Ala Ser Ser Thr Gly Leu Gln Cys Tyr Tyr Val
                 100                 105                 110

Tyr Asp His Ser Gly Glu Ala Val Lys Gly Ile Gln Asp Ala Asp Ser
         115                 120                 125

Ile Met Val Gln Ser Gly Leu Asp Gly Asp Ser Thr Leu Ser Gly Gly
         130                 135                 140

Asp Asn Glu Ser Glu Asn Ser Asp Val Asp Ile Gly Glu Pro Asp Thr
145                 150                 155                 160

Glu Gly Tyr Ala Ile Thr Asp Arg Gly Ser Ala Pro Ile Ser Met Gly
                 165                 170                 175

Phe Arg Ala Ser Asp Val Glu Thr Ala Glu Gly Glu Ile His Glu
                 180                 185                 190

Leu Leu Arg Leu Gln Ser Arg Gly Asn Asn Phe Pro Lys Leu Gly Lys
             195                 200                 205

Thr Leu Asn Val Pro Pro Pro Asp Pro Gly Arg Ala Ser Thr Ser
     210                 215                 220

Gly Thr Pro Ile Lys Lys Gly Thr Glu Arg Arg Leu Ala Ser Phe Gly
225                 230                 235                 240

Thr Glu Ile Ala Ser Leu Leu Thr Gly Gly Ala Thr Gln Cys Ala Arg
                 245                 250                 255

Lys Ser Pro Ser Glu Pro Ser Gly Pro Gly Ala Pro Ala Gly Asn Val
             260                 265                 270

Pro Glu Tyr Val Ser Asn Ala Ala Leu Ile Gln Glu Trp Thr Pro Glu
         275                 280                 285

Ser Gly Thr Thr Ile Ser Pro Arg Ser Gln Asn Asn Glu Glu Gly Gly
     290                 295                 300

Asp Tyr Tyr Asp Asp Glu Leu Phe Ser Asp Val Gln Asp Ile Lys Thr
305                 310                 315                 320

Ala Leu Ala Lys Ile His Glu Asp Asn Gln Lys Ile Ile Ser Lys Leu
                 325                 330                 335

Glu Ser Leu Leu Leu Leu Lys Gly Glu Val Glu Ser Ile Lys Lys Gln
         340                 345                 350

Ile Asn Arg Gln Asn Ile Ser Ile Ser Thr Leu Glu Gly His Leu Ser
         355                 360                 365

Ser Ile Met Ile Ala Ile Pro Gly Leu Gly Lys Asp Pro Asn Asp Pro
370                 375                 380

Thr Ala Asp Val Glu Ile Asn Pro Asp Leu Lys Pro Ile Ile Gly Arg
385                 390                 395                 400

Asp Ser Gly Arg Ala Leu Ala Glu Val Leu Lys Lys Pro Val Ala Ser
                 405                 410                 415

Arg Gln Leu Gln Gly Met Thr Asn Gly Arg Thr Ser Ser Arg Gly Gln
             420                 425                 430

Leu Leu Lys Glu Phe Gln Pro Lys Pro Ile Gly Lys Lys Met Ser Ser
         435                 440                 445
```

```
Ala  Val  Gly  Phe  Val  Pro  Asp  Thr  Gly  Pro  Ala  Ser  Arg  Ser  Val  Ile
     450                 455                 460

Arg  Ser  Ile  Ile  Lys  Ser  Ser  Arg  Leu  Glu  Glu  Asp  Arg  Lys  Arg  Tyr
465                      470                 475                           480

Leu  Met  Thr  Leu  Leu  Asp  Asp  Ile  Lys  Gly  Ala  Asn  Asp  Leu  Ala  Lys
                    485                 490                           495

Phe  His  Gln  Met  Leu  Met  Lys  Ile  Ile  Met  Lys
               500                 505
```

( 2 ) INFORMATION FOR SEQ ID NO:4:

( i ) SEQUENCE CHARACTERISTICS:
        ( A ) LENGTH: 335 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Thr  Glu  Ile  Tyr  Asp  Phe  Asp  Lys  Ser  Ala  Trp  Asp  Ile  Lys  Gly
 1                  5                   10                           15

Ser  Ile  Ala  Pro  Ile  Gln  Pro  Thr  Thr  Tyr  Ser  Asp  Gly  Arg  Leu  Val
               20                 25                            30

Pro  Gln  Val  Arg  Val  Ile  Asp  Pro  Gly  Leu  Gly  Asp  Arg  Lys  Asp  Glu
               35                 40                            45

Cys  Phe  Met  Tyr  Met  Ser  Leu  Leu  Gly  Val  Val  Glu  Asp  Ser  Asp  Pro
     50                      55                      60

Leu  Gly  Pro  Pro  Ile  Gly  Arg  Ala  Phe  Gly  Ser  Leu  Pro  Leu  Gly  Val
 65                      70                 75                            80

Gly  Arg  Ser  Thr  Ala  Lys  Pro  Glu  Lys  Leu  Leu  Lys  Glu  Ala  Thr  Glu
               85                 90                            95

Leu  Asp  Ile  Val  Val  Arg  Arg  Thr  Ala  Gly  Leu  Asn  Glu  Lys  Leu  Val
               100                105                           110

Phe  Tyr  Asn  Asn  Thr  Pro  Leu  Thr  Leu  Leu  Thr  Pro  Trp  Arg  Lys  Val
          115                 120                           125

Leu  Thr  Thr  Gly  Ser  Val  Phe  Asn  Ala  Asn  Gln  Val  Cys  Asn  Ala  Val
     130                     135                 140

Asn  Leu  Ile  Pro  Leu  Asp  Thr  Pro  Gln  Arg  Phe  Arg  Val  Val  Tyr  Met
145                      150                 155                          160

Ser  Ile  Thr  Arg  Leu  Ser  Asp  Asn  Gly  Tyr  Tyr  Thr  Val  Pro  Arg  Arg
                    165                 170                      175

Met  Leu  Glu  Phe  Arg  Ser  Val  Asn  Ala  Val  Ala  Phe  Asn  Leu  Leu  Val
               180                 185                      190

Thr  Leu  Arg  Ile  Asp  Lys  Ala  Ile  Gly  Pro  Gly  Lys  Ile  Ile  Asp  Asn
          195                 200                      205

Thr  Glu  Gln  Leu  Pro  Glu  Ala  Thr  Phe  Met  Val  His  Ile  Gly  Asn  Phe
     210                     215                 220

Arg  Arg  Lys  Lys  Ser  Glu  Val  Tyr  Ser  Ala  Asp  Tyr  Cys  Lys  Met  Lys
225                      230                 235                          240

Ile  Glu  Lys  Met  Gly  Leu  Val  Phe  Ala  Leu  Gly  Gly  Ile  Gly  Gly  Thr
               245                 250                      255

Ser  Leu  His  Ile  Arg  Ser  Thr  Gly  Lys  Met  Ser  Lys  Thr  Leu  His  Ala
               260                 265                      270

Gln  Leu  Gly  Phe  Lys  Lys  Thr  Leu  Cys  Tyr  Pro  Leu  Met  Asp  Ile  Asn
          275                 280                      285

Glu  Asp  Leu  Asn  Arg  Leu  Leu  Trp  Arg  Ser  Arg  Cys  Lys  Ile  Val  Arg
```

290                     295                     300
Ile  Gln  Ala  Val  Leu  Gln  Pro  Ser  Val  Pro  Gln  Glu  Phe  Arg  Ile  Tyr
305                     310                     315                     320

Asp  Asp  Val  Ile  Ile  Asn  Asp  Gln  Gly  Leu  Phe  Lys  Val  Leu
                    325                     330                     335

( 2 ) INFORMATION FOR SEQ ID NO:5:

( i ) SEQUENCE CHARACTERISTICS:
        ( A ) LENGTH: 550 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

Met  Gly  Leu  Lys  Val  Asn  Val  Ser  Ala  Ile  Phe  Met  Ala  Val  Leu  Leu
 1               5                       10                      15

Thr  Leu  Gln  Thr  Pro  Thr  Gly  Gln  Ile  His  Trp  Gly  Asn  Leu  Ser  Lys
               20                      25                      30

Ile  Gly  Val  Val  Gly  Ile  Gly  Ser  Ala  Ser  Tyr  Lys  Val  Met  Thr  Arg
          35                      40                      45

Ser  Ser  His  Gln  Ser  Leu  Val  Ile  Lys  Leu  Met  Pro  Asn  Ile  Thr  Leu
 50                     55                      60

Leu  Asn  Asn  Cys  Thr  Arg  Val  Glu  Ile  Ala  Glu  Tyr  Arg  Arg  Leu  Leu
65                      70                      75                      80

Arg  Thr  Val  Leu  Glu  Pro  Ile  Arg  Asp  Ala  Leu  Asn  Ala  Met  Thr  Gln
                    85                      90                      95

Asn  Ile  Arg  Pro  Val  Gln  Ser  Val  Ala  Ser  Ser  Arg  Arg  His  Lys  Arg
               100                     105                     110

Phe  Ala  Gly  Val  Val  Leu  Ala  Gly  Ala  Ala  Leu  Gly  Val  Ala  Thr  Ala
          115                     120                     125

Ala  Gln  Ile  Thr  Ala  Gly  Ile  Ala  Leu  His  Gln  Ser  Met  Leu  Asn  Ser
130                     135                     140

Gln  Ala  Ile  Asp  Asn  Leu  Arg  Ala  Ser  Leu  Glu  Thr  Thr  Asn  Gln  Ala
145                     150                     155                     160

Ile  Glu  Ala  Ile  Arg  Gln  Ala  Gly  Gln  Glu  Met  Ile  Leu  Ala  Val  Gln
                    165                     170                     175

Gly  Val  Gln  Asp  Tyr  Ile  Asn  Asn  Glu  Leu  Ile  Pro  Ser  Met  Asn  Gln
               180                     185                     190

Leu  Ser  Cys  Asp  Leu  Ile  Gly  Gln  Lys  Leu  Gly  Leu  Lys  Leu  Leu  Arg
          195                     200                     205

Tyr  Tyr  Thr  Glu  Ile  Leu  Ser  Leu  Phe  Gly  Pro  Ser  Leu  Arg  Asp  Pro
210                     215                     220

Ile  Ser  Ala  Glu  Ile  Ser  Ile  Gln  Ala  Leu  Ser  Tyr  Ala  Leu  Gly  Gly
225                     230                     235                     240

Asp  Ile  Asn  Lys  Val  Leu  Glu  Lys  Leu  Gly  Tyr  Ser  Gly  Gly  Asp  Leu
                    245                     250                     255

Leu  Gly  Ile  Leu  Glu  Ser  Arg  Gly  Ile  Lys  Ala  Arg  Ile  Thr  His  Val
               260                     265                     270

Asp  Thr  Glu  Ser  Tyr  Leu  Ile  Val  Leu  Ser  Ile  Ala  Tyr  Pro  Thr  Leu
          275                     280                     285

Ser  Glu  Ile  Lys  Gly  Val  Ile  Val  His  Arg  Leu  Glu  Gly  Val  Ser  Tyr
290                     295                     300

Asn  Ile  Gly  Ser  Gln  Glu  Trp  Tyr  Thr  Thr  Val  Pro  Lys  Tyr  Val  Ala
305                     310                     315                     320

-continued

| | | | | | | | | | | | | | | |
|---|---|---|---|---|---|---|---|---|---|---|---|---|---|---|
| Thr | Gln | Gly | Tyr | Leu | Ile | Ser | Asn | Phe | Asp | Glu | Ser | Ser | Cys | Thr | Phe |
| | | | | 325 | | | | | 330 | | | | | 335 | |

| Met | Pro | Glu | Gly | Thr | Val | Cys | Ser | Gln | Asn | Ala | Leu | Tyr | Pro | Met | Ser |
| | | | 340 | | | | | 345 | | | | | 350 | | |

| Pro | Leu | Leu | Gln | Glu | Cys | Leu | Arg | Gly | Ser | Thr | Lys | Ser | Cys | Ala | Arg |
| | | 355 | | | | | 360 | | | | | 365 | | | |

| Thr | Leu | Val | Ser | Gly | Ser | Phe | Gly | Asn | Arg | Phe | Ile | Leu | Ser | Gln | Gly |
| | 370 | | | | | 375 | | | | | 380 | | | | |

| Asn | Leu | Ile | Ala | Asn | Cys | Ala | Ser | Ile | Leu | Cys | Lys | Cys | Tyr | Thr | Thr |
| 385 | | | | | 390 | | | | | 395 | | | | | 400 |

| Gly | Thr | Ile | Ile | Asn | Gln | Asp | Pro | Asp | Lys | Ile | Leu | Thr | Tyr | Ile | Ala |
| | | | | 405 | | | | | 410 | | | | | 415 | |

| Ala | Asp | His | Cys | Pro | Val | Val | Glu | Val | Asn | Gly | Val | Thr | Ile | Gln | Val |
| | | | 420 | | | | | 425 | | | | | 430 | | |

| Gly | Ser | Arg | Arg | Tyr | Pro | Asp | Ala | Val | Tyr | Leu | His | Arg | Ile | Asp | Leu |
| | | | 435 | | | | | 440 | | | | | 445 | | |

| Gly | Pro | Pro | Ile | Leu | Leu | Glu | Arg | Leu | Asp | Val | Gly | Thr | Asn | Leu | Gly |
| | | 450 | | | | | 455 | | | | | 460 | | | |

| Asn | Ala | Ile | Ala | Lys | Leu | Glu | Asp | Ala | Lys | Glu | Leu | Leu | Glu | Ser | Ser |
| 465 | | | | | 470 | | | | | 475 | | | | | 480 |

| Asp | Gln | Ile | Leu | Arg | Ser | Met | Lys | Gly | Leu | Ser | Ser | Thr | Cys | Ile | Val |
| | | | | 485 | | | | | 490 | | | | | 495 | |

| Tyr | Ile | Leu | Ile | Ala | Val | Cys | Leu | Gly | Gly | Leu | Ile | Gly | Ile | Pro | Ala |
| | | | 500 | | | | | 505 | | | | | 510 | | |

| Leu | Ile | Cys | Cys | Cys | Arg | Gly | Arg | Cys | Asn | Lys | Lys | Gly | Glu | Gln | Val |
| | | | 515 | | | | | 520 | | | | | 525 | | |

| Gly | Met | Ser | Arg | Pro | Gly | Leu | Lys | Pro | Asp | Leu | Thr | Gly | Thr | Ser | Lys |
| | | 530 | | | | | 535 | | | | | 540 | | | |

| Ser | Tyr | Val | Arg | Ser | Leu | | | | | | | | | | |
| 545 | | | | | 550 | | | | | | | | | | |

( 2 ) INFORMATION FOR SEQ ID NO:6:

( i ) SEQUENCE CHARACTERISTICS:
        ( A ) LENGTH: 617 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Ser | Pro | Gln | Arg | Asp | Arg | Ile | Asn | Ala | Phe | Tyr | Lys | Asp | Asn | Pro |
| 1 | | | | 5 | | | | | 10 | | | | | 15 | |

| His | Pro | Lys | Gly | Ser | Arg | Ile | Val | Ile | Asn | Arg | Glu | His | Leu | Met | Ile |
| | | | 20 | | | | | 25 | | | | | 30 | | |

| Asp | Arg | Pro | Tyr | Val | Leu | Leu | Ala | Val | Leu | Phe | Val | Met | Phe | Leu | Ser |
| | | 35 | | | | | 40 | | | | | 45 | | | |

| Leu | Ile | Gly | Leu | Leu | Ala | Ile | Ala | Gly | Ile | Arg | Leu | His | Arg | Ala | Ala |
| | 50 | | | | | 55 | | | | | 60 | | | | |

| Ile | Tyr | Thr | Ala | Glu | Ile | His | Lys | Ser | Leu | Ser | Thr | Asn | Leu | Asp | Val |
| 65 | | | | | 70 | | | | | 75 | | | | | 80 |

| Thr | Asn | Ser | Ile | Glu | His | Gln | Val | Lys | Asp | Val | Leu | Thr | Pro | Leu | Phe |
| | | | | 85 | | | | | 90 | | | | | 95 | |

| Lys | Ile | Ile | Gly | Asp | Glu | Val | Gly | Leu | Arg | Thr | Pro | Gln | Arg | Phe | Thr |
| | | | 100 | | | | | 105 | | | | | 110 | | |

| Asp | Leu | Val | Lys | Phe | Ile | Ser | Asp | Lys | Ile | Lys | Phe | Leu | Asn | Pro | Asp |
| | | 115 | | | | | 120 | | | | | 125 | | | |

-continued

| | | | | | | | | | | | | | |
|---|---|---|---|---|---|---|---|---|---|---|---|---|---|
| Arg | Glu | Tyr | Asp | Phe | Arg | Asp | Leu | Thr | Trp | Cys | Met | Asn | Pro | Pro | Glu |
| | 130 | | | | 135 | | | | | 140 | | | |
| Arg | Ile | Lys | Leu | Asp | Tyr | Asp | Gln | Tyr | Cys | Ala | Asp | Val | Ala | Ala | Glu |
| 145 | | | | | 150 | | | | 155 | | | | | 160 |
| Glu | Leu | Met | Asn | Ala | Leu | Val | Asn | Ser | Thr | Leu | Leu | Glu | Thr | Arg | Thr |
| | | | | 165 | | | | | 170 | | | | | 175 |
| Thr | Asn | Gln | Phe | Leu | Ala | Val | Ser | Lys | Gly | Asn | Cys | Ser | Gly | Pro | Thr |
| | | | 180 | | | | | 185 | | | | | 190 | |
| Thr | Ile | Arg | Gly | Gln | Phe | Ser | Asn | Met | Ser | Leu | Ser | Leu | Leu | Asp | Leu |
| | | 195 | | | | | 200 | | | | 205 | | | |
| Tyr | Leu | Gly | Arg | Gly | Tyr | Asn | Val | Ser | Ser | Ile | Val | Thr | Met | Thr | Ser |
| | 210 | | | | | 215 | | | | 220 | | | | |
| Gln | Gly | Met | Tyr | Gly | Gly | Thr | Tyr | Leu | Val | Glu | Lys | Pro | Asn | Leu | Ser |
| 225 | | | | | 230 | | | | | 235 | | | | | 240 |
| Ser | Lys | Arg | Ser | Glu | Leu | Ser | Gln | Leu | Ser | Met | Tyr | Arg | Val | Phe | Glu |
| | | | | 245 | | | | | 250 | | | | | 255 |
| Val | Gly | Val | Ile | Arg | Asn | Pro | Gly | Leu | Gly | Ala | Pro | Val | Phe | His | Met |
| | | | 260 | | | | 265 | | | | | 270 | | |
| Thr | Asn | Tyr | Leu | Glu | Gln | Pro | Val | Ser | Asn | Asp | Leu | Ser | Asn | Cys | Met |
| | | 275 | | | | | 280 | | | | 285 | | | |
| Val | Ala | Leu | Gly | Glu | Leu | Lys | Leu | Ala | Ala | Leu | Cys | His | Arg | Glu | Asp |
| | 290 | | | | 295 | | | | | 300 | | | | |
| Ser | Ile | Thr | Ile | Pro | Tyr | Gln | Gly | Ser | Gly | Lys | Gly | Val | Ser | Phe | Gln |
| 305 | | | | | 310 | | | | 315 | | | | | 320 |
| Leu | Val | Lys | Leu | Gly | Val | Trp | Lys | Ser | Pro | Thr | Asp | Met | Gln | Ser | Trp |
| | | | | 325 | | | | | 330 | | | | | 335 |
| Val | Thr | Leu | Ser | Thr | Asp | Asp | Pro | Val | Ile | Asp | Arg | Leu | Tyr | Leu | Ser |
| | | | 340 | | | | 345 | | | | | 350 | | |
| Ser | His | Arg | Gly | Val | Ile | Ala | Asp | Asn | Gln | Ala | Lys | Trp | Ala | Val | Pro |
| | | 355 | | | | | 360 | | | | 365 | | | |
| Thr | Thr | Arg | Thr | Asp | Asp | Lys | Leu | Arg | Met | Glu | Thr | Cys | Phe | Gln | Gln |
| | 370 | | | | 375 | | | | | 380 | | | | |
| Ala | Cys | Lys | Gly | Lys | Ile | Gln | Ala | Leu | Cys | Glu | Asn | Pro | Glu | Trp | Ala |
| 385 | | | | | 390 | | | | 395 | | | | | 400 |
| Pro | Leu | Lys | Asp | Asn | Arg | Ile | Pro | Ser | Tyr | Gly | Val | Leu | Ser | Val | Asp |
| | | | | 405 | | | | 410 | | | | | 415 | |
| Leu | Ser | Leu | Thr | Val | Glu | Leu | Lys | Ile | Lys | Ile | Ala | Ser | Gly | Phe | Gly |
| | | | 420 | | | | 425 | | | | | 430 | | |
| Pro | Leu | Ile | Thr | His | Gly | Ser | Gly | Met | Asp | Leu | Tyr | Lys | Ser | Asn | His |
| | | 435 | | | | 440 | | | | | 445 | | | |
| Asn | Asn | Val | Tyr | Trp | Leu | Thr | Ile | Pro | Pro | Met | Lys | Asn | Leu | Ala | Leu |
| 450 | | | | | 455 | | | | 460 | | | | | |
| Gly | Val | Ile | Asn | Thr | Leu | Glu | Trp | Ile | Pro | Arg | Phe | Lys | Val | Ser | Pro |
| 465 | | | | | 470 | | | | 475 | | | | | 480 |
| Tyr | Leu | Phe | Asn | Val | Pro | Ile | Lys | Glu | Ala | Gly | Glu | Asp | Cys | His | Ala |
| | | | | 485 | | | | 490 | | | | 495 | | |
| Pro | Thr | Tyr | Leu | Pro | Ala | Glu | Val | Asp | Gly | Asp | Val | Lys | Leu | Ser | Ser |
| | | | 500 | | | | 505 | | | | 510 | | | |
| Asn | Leu | Val | Ile | Leu | Pro | Gly | Gln | Asp | Leu | Gln | Tyr | Val | Leu | Ala | Thr |
| | | 515 | | | | 520 | | | | | 525 | | | |
| Tyr | Asp | Thr | Ser | Arg | Val | Glu | His | Ala | Val | Val | Tyr | Tyr | Val | Tyr | Ser |
| | 530 | | | | | 535 | | | | 540 | | | | |
| Pro | Ser | Arg | Ser | Phe | Ser | Tyr | Phe | Tyr | Pro | Phe | Arg | Leu | Pro | Ile | Lys |

```
545                     550                     555                     560
Gly  Val  Pro  Ile  Glu  Leu  Gln  Val  Glu  Cys  Phe  Thr  Trp  Asp  Gln  Lys
                    565                     570                     575

Leu  Trp  Cys  Arg  His  Phe  Cys  Val  Leu  Ala  Asp  Ser  Glu  Ser  Gly  Gly
               580                     585                     590

His  Ile  Thr  His  Ser  Gly  Met  Val  Gly  Met  Gly  Val  Ser  Cys  Thr  Val
               595                     600                     605

Thr  Arg  Glu  Asp  Gly  Thr  Asn  Arg  Arg
          610                     615
```

( 2 ) INFORMATION FOR SEQ ID NO:7:

( i ) SEQUENCE CHARACTERISTICS:
        ( A ) LENGTH: 2183 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Asp  Ser  Leu  Ser  Val  Asn  Gln  Ile  Leu  Tyr  Pro  Glu  Val  His  Leu
 1                   5                      10                      15

Asp  Ser  Pro  Ile  Val  Thr  Asn  Lys  Ile  Val  Ala  Ile  Leu  Glu  Tyr  Ala
                20                      25                      30

Arg  Val  Pro  His  Ala  Tyr  Ser  Leu  Glu  Asp  Pro  Thr  Leu  Cys  Gln  Asn
               35                      40                      45

Ile  Lys  His  Arg  Leu  Lys  Asn  Gly  Phe  Ser  Asn  Gln  Met  Ile  Ile  Asn
     50                       55                      60

Asn  Val  Glu  Val  Gly  Asn  Val  Ile  Lys  Ser  Lys  Leu  Arg  Ser  Tyr  Pro
 65                      70                      75                      80

Ala  His  Ser  His  Ile  Pro  Tyr  Pro  Asn  Cys  Asn  Gln  Asp  Leu  Phe  Asn
               85                      90                      95

Ile  Glu  Asp  Lys  Glu  Ser  Thr  Arg  Lys  Ile  Arg  Glu  Leu  Leu  Lys  Lys
               100                     105                     110

Gly  Asn  Ser  Leu  Tyr  Ser  Lys  Val  Ser  Asp  Lys  Val  Phe  Gln  Cys  Leu
               115                     120                     125

Arg  Asp  Thr  Asn  Ser  Arg  Leu  Gly  Leu  Gly  Ser  Glu  Leu  Arg  Glu  Asp
     130                     135                     140

Ile  Lys  Glu  Lys  Val  Ile  Asn  Leu  Gly  Val  Tyr  Met  His  Ser  Ser  Gln
145                      150                     155                     160

Trp  Phe  Glu  Pro  Phe  Leu  Phe  Trp  Phe  Thr  Val  Lys  Thr  Glu  Met  Arg
                165                     170                     175

Ser  Val  Ile  Lys  Ser  Gln  Thr  His  Thr  Cys  His  Arg  Arg  Arg  His  Thr
               180                     185                     190

Pro  Val  Phe  Phe  Thr  Gly  Ser  Ser  Val  Glu  Leu  Leu  Ile  Ser  Arg  Asp
               195                     200                     205

Leu  Val  Ala  Ile  Ile  Ser  Lys  Glu  Ser  Gln  His  Val  Tyr  Tyr  Leu  Thr
     210                     215                     220

Phe  Glu  Leu  Val  Leu  Met  Tyr  Cys  Asp  Val  Ile  Glu  Gly  Arg  Leu  Met
225                      230                     235                     240

Thr  Glu  Thr  Ala  Met  Thr  Ile  Asp  Ala  Arg  Tyr  Thr  Glu  Leu  Leu  Gly
                245                     250                     255

Arg  Val  Arg  Tyr  Met  Trp  Lys  Leu  Ile  Asp  Gly  Phe  Phe  Pro  Ala  Leu
               260                     265                     270

Gly  Asn  Pro  Thr  Tyr  Gln  Ile  Val  Ala  Met  Leu  Glu  Pro  Leu  Ser  Leu
               275                     280                     285
```

| | | | | | | | | | | | | | | |
|---|---|---|---|---|---|---|---|---|---|---|---|---|---|---|
| Ala | Tyr 290 | Leu | Gln | Leu | Arg 295 | Asp | Ile | Thr | Val | Glu 300 | Leu | Arg | Gly | Ala | Phe |
| Leu 305 | Asn | His | Cys | Phe | Thr 310 | Glu | Ile | His | Asp | Val 315 | Leu | Asp | Gln | Asn | Gly 320 |
| Phe | Ser | Asp | Glu | Gly 325 | Thr | Tyr | His | Glu | Leu 330 | Ile | Glu | Ala | Leu | Asp 335 | Tyr |
| Ile | Phe | Ile | Thr 340 | Asp | Asp | Ile | His | Leu 345 | Thr | Gly | Glu | Ile | Phe 350 | Ser | Phe |
| Phe | Arg | Ser 355 | Phe | Gly | His | Pro | Arg 360 | Leu | Glu | Ala | Val | Thr 365 | Ala | Ala | Glu |
| Asn | Val 370 | Arg | Lys | Tyr | Met | Asn 375 | Gln | Pro | Lys | Val | Ile 380 | Val | Tyr | Glu | Thr |
| Leu 385 | Met | Lys | Gly | His | Ala 390 | Ile | Phe | Cys | Gly | Ile 395 | Ile | Ile | Asn | Gly | Tyr 400 |
| Arg | Asp | Arg | His | Gly 405 | Gly | Ser | Trp | Pro | Pro 410 | Leu | Thr | Leu | Pro | Leu 415 | His |
| Ala | Ala | Asp | Thr 420 | Ile | Arg | Asn | Ala | Gln 425 | Ala | Ser | Gly | Glu | Gly 430 | Leu | Thr |
| His | Glu | Gln 435 | Cys | Val | Asp | Asn | Trp 440 | Lys | Ser | Phe | Ala | Gly 445 | Val | Lys | Phe |
| Gly | Cys 450 | Phe | Met | Pro | Leu | Ser 455 | Leu | Asp | Ser | Asp | Leu 460 | Thr | Met | Tyr | Leu |
| Lys 465 | Asp | Lys | Ala | Leu | Ala 470 | Ala | Leu | Gln | Arg | Glu 475 | Trp | Asp | Ser | Val | Tyr 480 |
| Pro | Lys | Glu | Phe | Leu 485 | Arg | Tyr | Asp | Pro | Pro 490 | Lys | Gly | Thr | Gly | Ser 495 | Arg |
| Arg | Leu | Val | Asp 500 | Val | Phe | Leu | Asn | Asp 505 | Ser | Ser | Phe | Asp | Pro 510 | Tyr | Asp |
| Val | Ile | Met 515 | Tyr | Val | Val | Ser | Gly 520 | Ala | Tyr | Leu | His | Asp 525 | Pro | Glu | Phe |
| Asn | Leu 530 | Ser | Tyr | Ser | Leu | Lys 535 | Glu | Lys | Glu | Ile | Lys 540 | Glu | Thr | Gly | Arg |
| Leu 545 | Phe | Ala | Lys | Met | Thr 550 | Tyr | Lys | Met | Arg | Ala 555 | Cys | Gln | Val | Ile | Ala 560 |
| Glu | Asn | Leu | Ile | Ser 565 | Asn | Gly | Ile | Gly | Lys 570 | Tyr | Phe | Lys | Asp | Asn 575 | Gly |
| Met | Ala | Lys | Asp 580 | Glu | His | Asp | Leu | Thr 585 | Lys | Ala | Leu | His | Thr 590 | Leu | Ala |
| Val | Ser | Gly 595 | Val | Pro | Lys | Asp | Leu 600 | Lys | Glu | Ser | His | Arg 605 | Gly | Gly | Pro |
| Val | Leu | Lys 610 | Thr | Tyr | Ser | Arg | Ser 615 | Pro | Val | His | Thr 620 | Ser | Thr | Arg | Asn |
| Val | Arg 625 | Ala | Ala | Lys | Gly 630 | Phe | Ile | Gly | Phe | Pro 635 | Gln | Val | Ile | Arg | Gln 640 |
| Asp | Gln | Asp | Thr | Asp 645 | His | Pro | Glu | Asn | Met 650 | Glu | Ala | Tyr | Glu | Thr 655 | Val |
| Ser | Ala | Phe | Ile 660 | Thr | Thr | Asp | Leu | Lys 665 | Lys | Tyr | Cys | Leu | Asn 670 | Trp | Arg |
| Tyr | Glu | Thr 675 | Ile | Ser | Leu | Phe | Ala 680 | Gln | Arg | Leu | Asn | Glu 685 | Ile | Tyr | Gly |
| Leu | Pro 690 | Ser | Phe | Phe | Gln | Trp 695 | Leu | His | Lys | Arg | Leu 700 | Glu | Thr | Ser | Val |
| Leu 705 | Tyr | Val | Ser | Asp | Pro 710 | His | Cys | Pro | Pro | Asp 715 | Leu | Asp | Ala | His | Ile 720 |

Pro Leu Tyr Lys Val Pro Asn Asp Gln Ile Phe Ile Lys Tyr Pro Met
                725                 730                 735

Gly Gly Ile Glu Gly Tyr Cys Gln Lys Leu Trp Thr Ile Ser Thr Ile
            740                 745                 750

Pro Tyr Leu Tyr Leu Ala Ala Tyr Glu Ser Gly Val Arg Ile Ala Ser
        755                 760                 765

Leu Val Gln Gly Asp Asn Gln Thr Ile Ala Val Thr Lys Arg Val Pro
    770                 775                 780

Ser Thr Trp Pro Tyr Asn Leu Lys Lys Arg Glu Ala Ala Arg Val Thr
785                 790                 795                 800

Arg Asp Tyr Phe Val Ile Leu Arg Gln Arg Leu His Asp Ile Gly His
                805                 810                 815

His Leu Lys Ala Asn Glu Thr Ile Val Ser Ser His Phe Phe Val Tyr
            820                 825                 830

Ser Lys Gly Ile Tyr Tyr Asp Gly Leu Leu Val Ser Gln Ser Leu Lys
        835                 840                 845

Ser Ile Ala Arg Cys Val Phe Trp Ser Glu Thr Ile Val Asp Glu Thr
    850                 855                 860

Arg Ala Ala Cys Ser Asn Ile Ala Thr Thr Met Ala Lys Ser Ile Glu
865                 870                 875                 880

Arg Gly Tyr Asp Arg Tyr Leu Ala Tyr Ser Leu Asn Val Leu Lys Val
                885                 890                 895

Ile Gln Gln Ile Leu Ile Ser Leu Gly Phe Thr Ile Asn Ser Thr Met
            900                 905                 910

Thr Arg Asp Val Val Ile Pro Leu Leu Thr Asn Asn Asp Leu Leu Ile
        915                 920                 925

Arg Met Ala Leu Leu Pro Ala Pro Ile Gly Gly Met Asn Tyr Leu Asn
930                 935                 940

Met Ser Arg Leu Phe Val Arg Asn Ile Gly Asp Pro Val Thr Ser Ser
945                 950                 955                 960

Ile Ala Asp Leu Lys Arg Met Ile Leu Ala Ser Leu Met Pro Glu Glu
                965                 970                 975

Thr Leu His Gln Val Met Thr Gln Gln Pro Gly Asp Ser Ser Phe Leu
            980                 985                 990

Asp Trp Ala Ser Asp Pro Tyr Ser Ala Asn Leu Val Cys Val Gln Ser
        995                 1000                1005

Ile Thr Arg Leu Leu Lys Asn Ile Thr Ala Arg Phe Val Leu Ile His
    1010                1015                1020

Ser Pro Asn Pro Met Leu Lys Gly Leu Phe His Asp Ser Lys Glu
1025                1030                1035                1040

Glu Asp Glu Gly Leu Ala Ala Phe Leu Met Asp Arg His Ile Ile Val
                1045                1050                1055

Pro Arg Ala Ala His Glu Ile Leu Asp His Ser Val Thr Gly Ala Arg
            1060                1065                1070

Glu Ser Ile Ala Gly Met Leu Asp Thr Thr Lys Gly Leu Ile Arg Ala
        1075                1080                1085

Ser Met Arg Lys Gly Gly Leu Thr Ser Arg Val Ile Thr Arg Leu Ser
    1090                1095                1100

Asn Tyr Asp Tyr Glu Gln Phe Arg Ala Gly Met Val Leu Leu Thr Gly
1105                1110                1115                1120

Arg Lys Arg Asn Val Leu Ile Asp Lys Glu Ser Cys Ser Val Gln Leu
                1125                1130                1135

Ala Arg Ala Leu Arg Ser His Met Trp Ala Arg Leu Ala Arg Gly Arg

-continued

```
                    1140                       1145                       1150
Pro Ile Tyr Gly Leu Glu Val Pro Asp Val Leu Glu Ser Met Arg Gly
        1155                    1160                    1165
His Leu Ile Arg Arg His Glu Thr Cys Val Ile Cys Glu Cys Gly Ser
    1170                1175                    1180
Val Asn Tyr Gly Trp Phe Phe Val Pro Ser Gly Cys Gln Leu Asp Asp
1185                1190                    1195                    1200
Ile Asp Lys Glu Thr Ser Ser Leu Arg Val Pro Tyr Ile Gly Ser Thr
                1205                    1210                    1215
Thr Asp Glu Arg Thr Asp Met Lys Leu Ala Phe Val Arg Ala Pro Ser
            1220                    1225                    1230
Arg Ser Leu Arg Ser Ala Val Arg Ile Ala Thr Val Tyr Ser Trp Ala
            1235                    1240                    1245
Tyr Gly Asp Asp Asp Ser Ser Trp Asn Glu Ala Trp Leu Leu Ala Arg
            1250                    1255                    1260
Gln Arg Ala Asn Val Ser Leu Glu Glu Leu Arg Val Ile Thr Pro Ile
1265                    1270                    1275                    1280
Ser Thr Ser Thr Asn Leu Ala His Arg Leu Arg Asp Arg Ser Thr Gln
                1285                    1290                    1295
Val Lys Tyr Ser Gly Thr Ser Leu Val Arg Val Ala Arg Tyr Thr Thr
                1300                    1305                    1310
Ile Ser Asn Asp Asn Leu Ser Phe Val Ile Ser Asp Lys Lys Val Asp
            1315                    1320                    1325
Thr Asn Phe Ile Tyr Gln Gln Gly Met Leu Leu Gly Leu Gly Val Leu
            1330                    1335                    1340
Glu Thr Leu Phe Arg Leu Glu Lys Asp Thr Gly Ser Ser Asn Thr Val
1345                    1350                    1355                    1360
Leu His Leu His Val Glu Thr Asp Cys Cys Val Ile Pro Met Ile Asp
                1365                    1370                    1375
His Pro Arg Ile Pro Ser Ser Arg Lys Leu Glu Leu Arg Ala Glu Leu
                1380                    1385                    1390
Cys Thr Asn Pro Leu Ile Tyr Asp Asn Ala Pro Leu Ile Asp Arg Asp
            1395                    1400                    1405
Thr Thr Arg Leu Tyr Thr Gln Ser His Arg Arg His Leu Val Glu Phe
        1410                    1415                    1420
Val Thr Trp Ser Thr Pro Gln Leu Tyr His Ile Leu Ala Lys Ser Thr
1425                    1430                    1435                    1440
Ala Leu Ser Met Ile Asp Leu Val Thr Lys Phe Glu Lys Asp His Met
                1445                    1450                    1455
Asn Glu Ile Ser Ala Leu Ile Gly Asp Asp Ile Asn Ser Phe Ile
                1460                    1465                    1470
Thr Glu Phe Leu Val Ile Glu Pro Arg Leu Phe Thr Ile Tyr Leu Gly
            1475                    1480                    1485
Gln Cys Ala Ala Ile Asn Trp Ala Phe Asp Val His Tyr His Arg Pro
        1490                    1495                    1500
Ser Gly Lys Tyr Gln Met Gly Glu Leu Leu Ser Ser Phe Leu Ser Arg
1505                    1510                    1515                    1520
Met Ser Lys Gly Val Phe Lys Val Leu Val Asn Ala Leu Ser His Pro
                1525                    1530                    1535
Lys Ile Tyr Lys Lys Phe Trp His Cys Gly Ile Ile Glu Pro Ile His
                1540                    1545                    1550
Gly Pro Ser Leu Asp Ala Gln Asn Leu His Thr Thr Val Cys Asn Met
            1555                    1560                    1565
```

```
Val  Tyr  Thr  Cys  Tyr  Met  Thr  Tyr  Leu  Asp  Leu  Leu  Leu  Asn  Glu  Glu
          1570               1575                    1580

Leu  Glu  Glu  Phe  Thr  Phe  Leu  Leu  Cys  Glu  Ser  Asp  Glu  Asp  Val  Val
1585                1590                    1595                         1600

Pro  Asp  Arg  Phe  Asp  Asn  Ile  Gln  Ala  Lys  His  Leu  Cys  Val  Leu  Ala
               1605                    1610                         1615

Asp  Leu  Tyr  Cys  Gln  Pro  Gly  Ala  Cys  Pro  Pro  Ile  Arg  Gly  Leu  Arg
          1620                    1625                         1630

Pro  Val  Glu  Lys  Cys  Ala  Val  Leu  Thr  Asp  His  Ile  Lys  Ala  Glu  Ala
     1635                    1640                    1645

Arg  Leu  Ser  Pro  Ala  Gly  Ser  Ser  Trp  Asn  Ile  Asn  Pro  Ile  Ile  Val
          1650                    1655                    1660

Asp  His  Tyr  Ser  Cys  Ser  Leu  Thr  Tyr  Leu  Arg  Arg  Gly  Ser  Ile  Lys
1665                1670                    1675                         1680

Gln  Ile  Arg  Leu  Arg  Val  Asp  Pro  Gly  Phe  Ile  Phe  Asp  Ala  Leu  Ala
                    1685                    1690                    1695

Glu  Val  Asn  Val  Ser  Gln  Pro  Lys  Ile  Gly  Ser  Asn  Asn  Ile  Ser  Asn
               1700                    1705                    1710

Met  Ser  Ile  Lys  Ala  Phe  Arg  Pro  His  Asp  Asp  Val  Ala  Lys  Leu
          1715                    1720                    1725

Leu  Lys  Asp  Ile  Asn  Thr  Ser  Lys  His  Asn  Leu  Pro  Ile  Ser  Gly  Gly
          1730                    1735                    1740

Asn  Leu  Ala  Asn  Tyr  Glu  Ile  His  Ala  Phe  Arg  Arg  Ile  Gly  Leu  Asn
1745                1750                    1755                         1760

Ser  Ser  Ala  Cys  Tyr  Lys  Ala  Val  Glu  Ile  Ser  Thr  Leu  Ile  Arg  Arg
               1765                    1770                         1775

Cys  Leu  Glu  Pro  Gly  Glu  Asp  Gly  Leu  Phe  Leu  Gly  Glu  Gly  Ser  Gly
               1780                    1785                    1790

Ser  Met  Leu  Ile  Thr  Tyr  Lys  Glu  Ile  Leu  Lys  Leu  Asn  Lys  Cys  Phe
          1795                    1800                    1805

Tyr  Asn  Ser  Gly  Val  Ser  Ala  Asn  Ser  Arg  Ser  Gly  Gln  Arg  Glu  Leu
          1810                    1815                    1820

Ala  Pro  Tyr  Pro  Ser  Glu  Val  Gly  Leu  Val  Glu  His  Arg  Met  Gly  Val
1825                    1830                    1835                    1840

Gly  Asn  Ile  Val  Lys  Val  Leu  Phe  Asn  Gly  Arg  Pro  Glu  Val  Thr  Trp
                    1845                    1850                    1855

Val  Gly  Ser  Val  Asp  Cys  Phe  Asn  Phe  Ile  Val  Ser  Asn  Ile  Pro  Thr
               1860                    1865                    1870

Ser  Ser  Val  Gly  Phe  Ile  His  Ser  Asp  Ile  Glu  Thr  Leu  Pro  Asn  Lys
          1875                    1880                    1885

Asp  Thr  Ile  Glu  Lys  Leu  Glu  Glu  Leu  Ala  Ala  Ile  Leu  Ser  Met  Ala
          1890                    1895                    1900

Leu  Leu  Leu  Gly  Lys  Ile  Gly  Ser  Ile  Leu  Val  Ile  Lys  Leu  Met  Pro
1905                    1910                    1915                    1920

Phe  Ser  Gly  Asp  Phe  Val  Gln  Gly  Phe  Ile  Ser  Tyr  Val  Gly  Ser  Tyr
                    1925                    1930                    1935

Tyr  Arg  Glu  Val  Asn  Leu  Val  Tyr  Pro  Arg  Tyr  Ser  Asn  Phe  Ile  Ser
               1940                    1945                    1950

Thr  Glu  Ser  Tyr  Leu  Val  Met  Thr  Asp  Leu  Lys  Ala  Asn  Arg  Leu  Met
          1955                    1960                    1965

Asn  Pro  Glu  Lys  Ile  Lys  Gln  Gln  Ile  Ile  Glu  Ser  Ser  Val  Arg  Thr
          1970                    1975                    1980

Ser  Pro  Gly  Leu  Ile  Gly  His  Ile  Leu  Ser  Ile  Lys  Gln  Leu  Ser  Cys
1985                    1990                    1995                    2000
```

| | | | | | | | | | | | | | | |
|---|---|---|---|---|---|---|---|---|---|---|---|---|---|---|
|Ile|Gln|Ala|Ile|Val|Gly|Asp|Val|Val|Ser|Arg|Gly|Asp|Ile|Asn|Pro|
| | | | |2005| | |2010| | | | |2015| | |

Ile Gln Ala Ile Val Gly Asp Val Val Ser Arg Gly Asp Ile Asn Pro
                    2005              2010                    2015

Thr Leu Lys Lys Leu Thr Pro Ile Glu Gln Val Leu Ile Asn Cys Gly
                    2020              2025              2030

Leu Ala Ile Asn Gly Pro Lys Leu Cys Lys Glu Leu Ile His His Asp
                2035              2040              2045

Val Ala Ser Gly Gln Asp Gly Leu Leu Asn Ser Ile Leu Ile Leu Tyr
        2050              2055              2060

Arg Glu Leu Ala Arg Phe Lys Asp Asn Arg Arg Ser Gln Gln Gly Met
2065                2070              2075                2080

Phe His Ala Tyr Pro Val Leu Val Ser Ser Arg Gln Arg Glu Leu Ile
            2085              2090              2095

Ser Arg Ile Thr Arg Lys Phe Trp Gly His Ile Leu Leu Tyr Ser Gly
            2100              2105              2110

Asn Arg Lys Leu Ile Asn Lys Phe Ile Gln Asn Leu Lys Ser Gly Tyr
        2115              2120              2125

Leu Ile Leu Asp Leu His Gln Asn Ile Phe Val Lys Asn Leu Ser Lys
        2130              2135              2140

Ser Glu Lys Gln Ile Ile Met Thr Gly Gly Leu Lys Arg Glu Trp Val
2145                2150              2155              2160

Phe Lys Val Thr Val Lys Glu Thr Lys Glu Trp Tyr Lys Leu Val Gly
                2165              2170              2175

Tyr Ser Ala Leu Ile Lys Asp
            2180

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

TTAGGGATAT CCGAGATGGC CACAC                                        25

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

CTCGGAAGAA CAAGGCTCAG ACAC                                       24

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

GGAAGGACAC CTCTCAAGCA TCATG    25

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GCAGCCATCA GTTCCTCAAG    20

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GTCTACATCC TGATTGCAGT G    21

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GTCAACGAGG AAGATCCGTG AACTCCTCA    29

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GCACGATTTG ACTAAGGCAC TCCA    24

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

TGTCCTCATT GACAAAGAGT CATG    24

(2) INFORMATION FOR SEQ ID NO:16:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:16:

AGGTGCTTGT CAATGCTCTA AGCCA  25

( 2 ) INFORMATION FOR SEQ ID NO:17:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:17:

CTTATCGATG GCTCTGCTCC TGGGC  25

( 2 ) INFORMATION FOR SEQ ID NO:18:

( i ) SEQUENCE CHARACTERISTICS:
  ( A ) LENGTH: 31 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:18:

TGGAAGCTTA TCCAGAATCT CAAGTCCGGC T  31

( 2 ) INFORMATION FOR SEQ ID NO:19:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:19:

CTGTGAATTC TGCAGGATCC TTTTTTT  27